(12) United States Patent
Baska

(10) Patent No.: US 9,038,636 B2
(45) Date of Patent: May 26, 2015

(54) LARYNGEAL MASK

(76) Inventor: Kanag Baska, Strathfield (AU)

( * ) Notice: Subject to any disclaimer, the term of this patent is extended or adjusted under 35 U.S.C. 154(b) by 1293 days.

(21) Appl. No.: 12/675,346

(22) PCT Filed: Aug. 27, 2008

(86) PCT No.: PCT/AU2008/001259
§ 371 (c)(1),
(2), (4) Date: Oct. 18, 2010

(87) PCT Pub. No.: WO2009/026628
PCT Pub. Date: Mar. 5, 2009

(65) Prior Publication Data
US 2011/0023890 A1 Feb. 3, 2011

(30) Foreign Application Priority Data

Aug. 30, 2007 (AU) ................................ 2007904697
Apr. 4, 2008 (AU) ................................ 2008901607

(51) Int. Cl.
*A61M 16/00* (2006.01)
*A62B 9/06* (2006.01)
*A61M 16/04* (2006.01)

(52) U.S. Cl.
CPC ........... *A61M 16/04* (2013.01); *A61M 16/0409* (2014.02); *A61M 16/0415* (2014.02)

(58) Field of Classification Search
USPC ..................... 128/204.17, 200.26, 207.14–17
See application file for complete search history.

(56) References Cited

U.S. PATENT DOCUMENTS

| | | | |
|---|---|---|---|
| 4,509,514 A | 4/1985 | Brain | 128/207.15 |
| 5,282,464 A * | 2/1994 | Brain | 128/207.15 |
| 5,743,258 A * | 4/1998 | Sato et al. | 128/207.15 |
| 5,791,341 A * | 8/1998 | Bullard | 128/207.15 |
| 6,079,409 A * | 6/2000 | Brain | 128/200.26 |
| 6,119,695 A | 9/2000 | Augustine et al. | 128/207.15 |
| 6,546,931 B2 | 4/2003 | Lin | 128/207.15 |
| 6,705,318 B1 | 3/2004 | Brain | 128/207.14 |
| 2002/0069880 A1 | 6/2002 | Lin | 128/207.15 |
| 2003/0131845 A1* | 7/2003 | Lin | 128/200.26 |
| 2004/0187872 A1 | 9/2004 | Brain | 128/207.14 |
| 2005/0081861 A1 | 4/2005 | Nasir | 128/207.14 |
| 2006/0027238 A1 | 2/2006 | Lin | 128/207.15 |
| 2006/0207601 A1 | 9/2006 | Nasir | 128/207.14 |

FOREIGN PATENT DOCUMENTS

| | | |
|---|---|---|
| AU | 630433 | 9/1990 |
| GB | 2 111 394 | 7/1983 |
| WO | WO 2004/016308 A2 | 2/2004 |
| WO | WO 2005/011784 A1 | 2/2005 |

OTHER PUBLICATIONS

Written Opinion of the International Searching Authority; International Preliminary Report on Patentability and International Search Report; PCT/AU2008/001259; mailed Nov. 5, 2008.

* cited by examiner

*Primary Examiner* — Steven Douglas
*Assistant Examiner* — Colin W Stuart
(74) *Attorney, Agent, or Firm* — Winston & Strawn LLP

(57) ABSTRACT

A device for maintaining an airway in a patient comprises mask having a peripheral portion that forms a seal with the larynx when the mask is positioned in the laryngo pharynx to thereby prevent ingress of extraneous fluids into the larynx airway tube connected to or formed with the mask for passing gas to the larynx when the mask is properly inserted into the laryngo pharynx. The peripheral portion of the mask includes a soft, flexible portion that contacts tissues surrounding the laryngeal opening when the device is inserted into a patient, the soft, flexible portion being arranged whereby application of pressurized gas to the airway tube urges the soft, flexible portion into contact with the tissues surrounding the laryngeal opening or the pharyngeal wall.

16 Claims, 30 Drawing Sheets

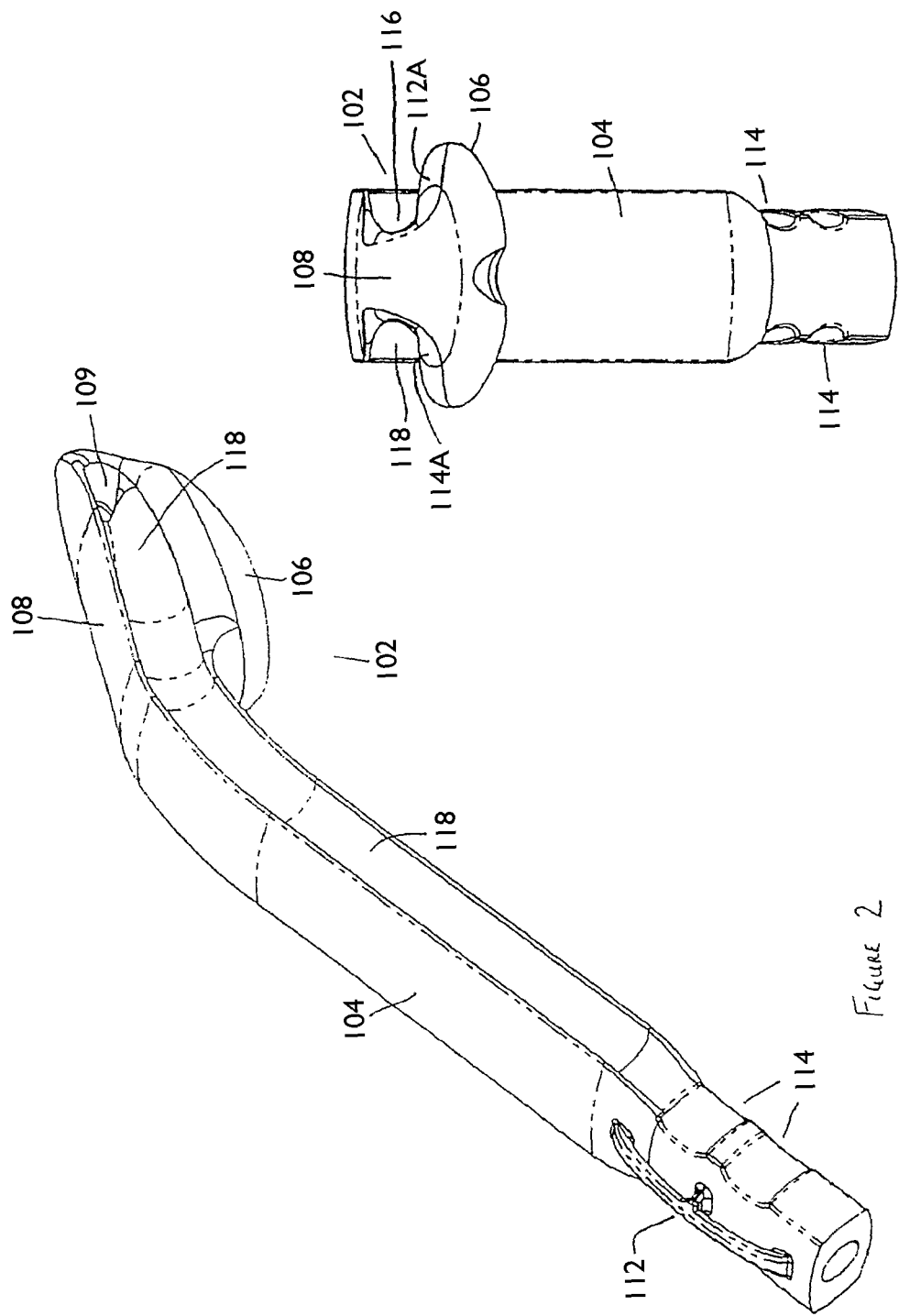

SECTION A-A

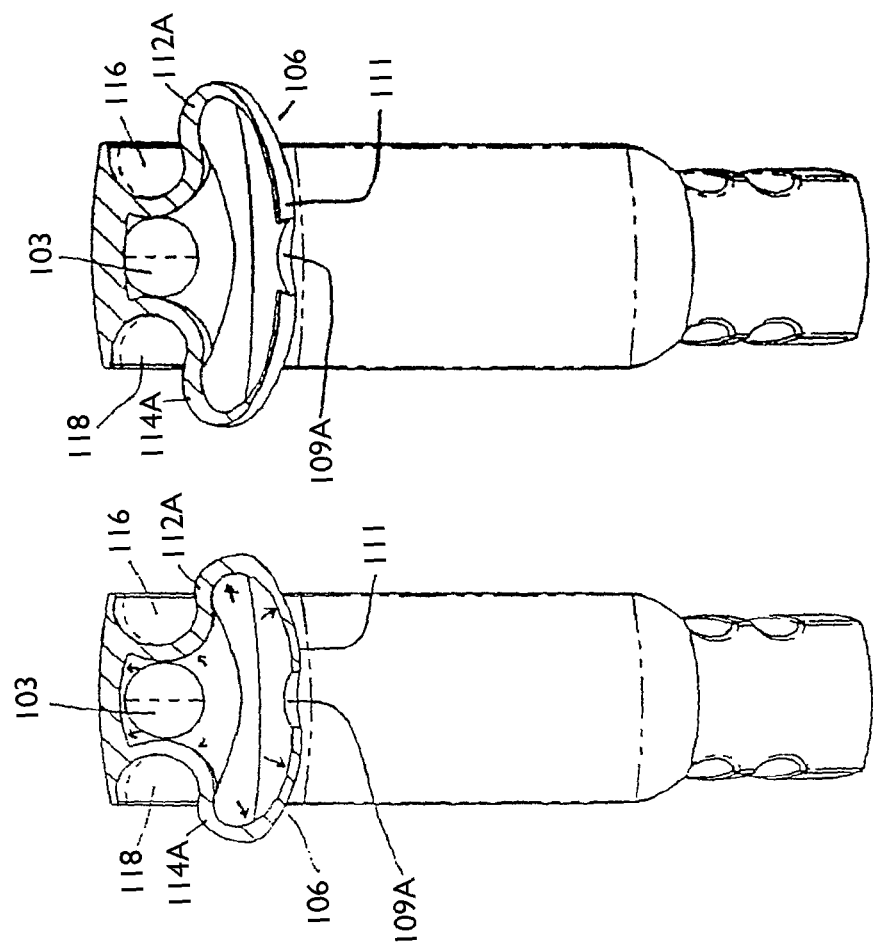

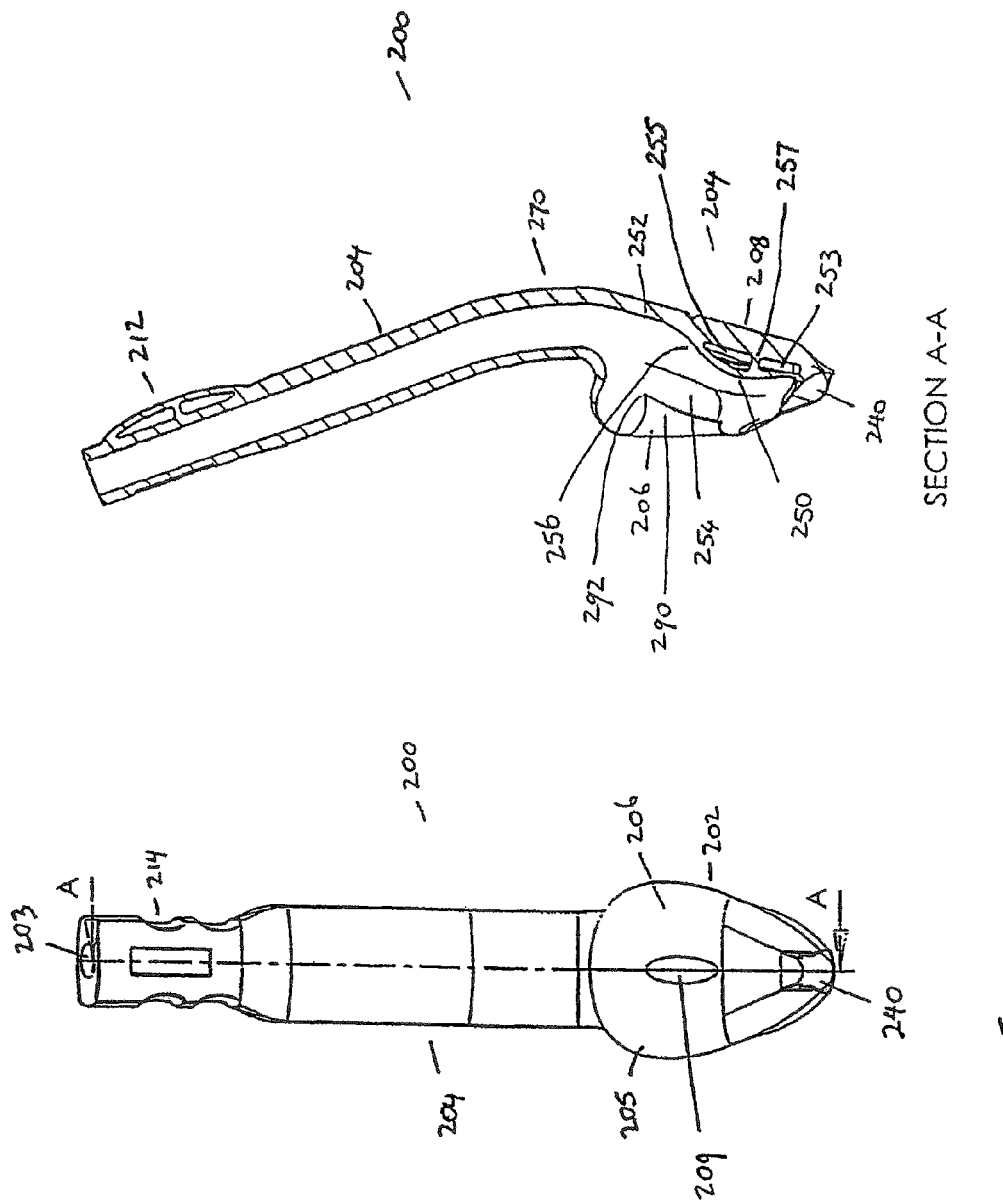

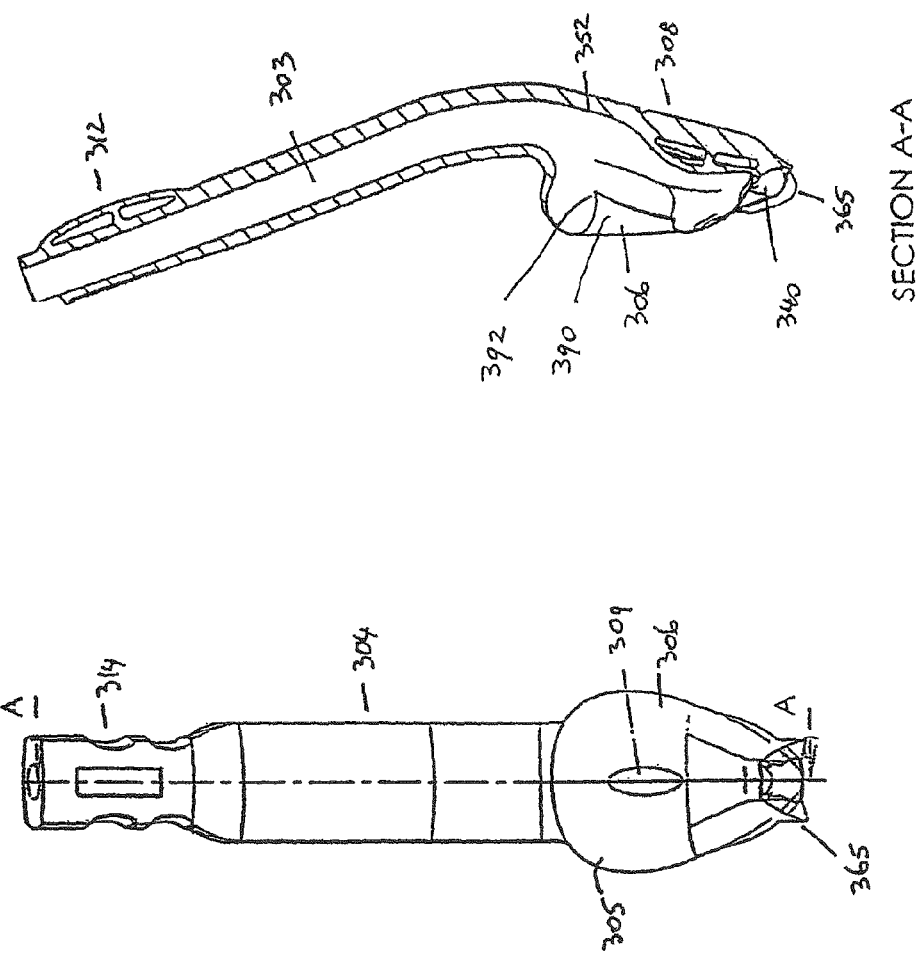

SECTION A-A
SCALE 1:2

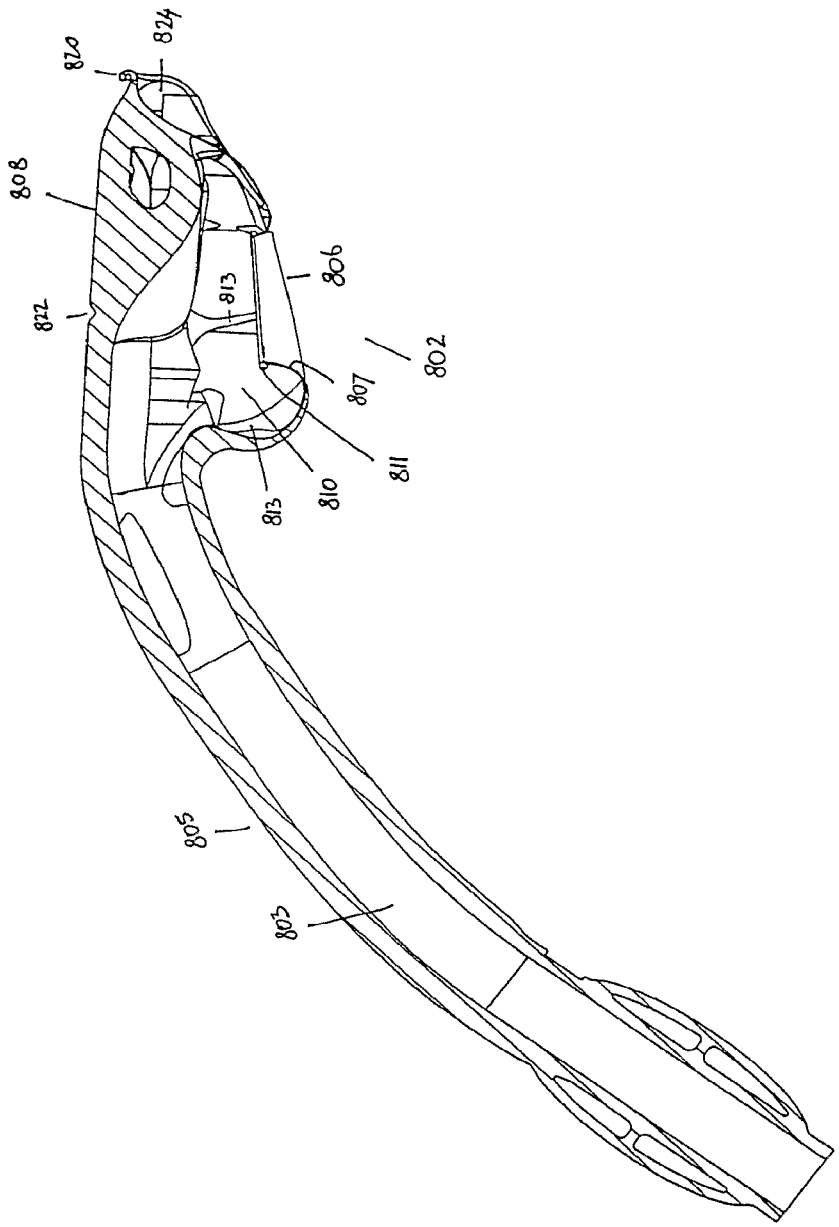
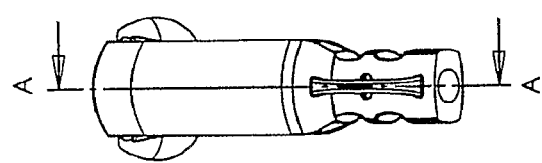
FIGURE 37A
FIGURE 37B

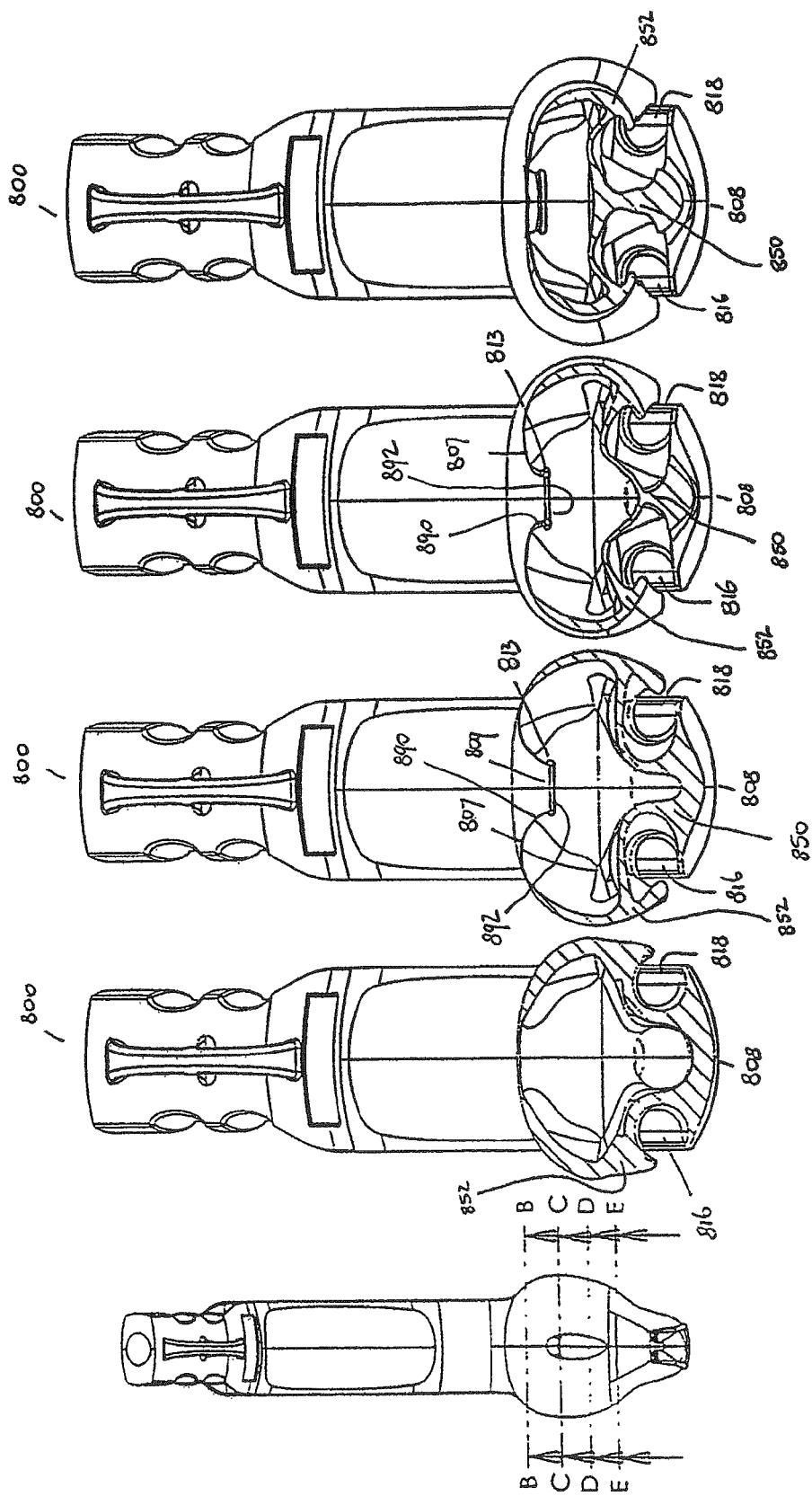

LARYNGEAL MASK

This application is a 371 filing of International Patent Application PCT/AU2008/001259 Aug. 27, 2008.

FIELD OF THE INVENTION

The present invention relates to a device for maintaining an airway in a patient. In preferred embodiments, the present invention relates to a laryngeal mask.

BACKGROUND OF THE INVENTION

Maintenance of a viable airway is critical to patient safety during surgical procedures conducted under general anaesthetic. Maintenance of a viable airway during such surgical procedures had, for many years, been achieved by insertion of an endo-tracheal tube into the patient. The endo-tracheal tube was typically inserted through the oral cavity or nasal cavity, into the larynx, through the vocal cords and into the trachea. As the endo-tracheal tube had to be inserted through the vocal cords, difficulty was often experienced in correctly positioning the endo-tracheal tube.

British patent no. 2,111,394 (which corresponds to U.S. Pat. No. 4,509,514) describes a device for maintaining an airway in a patient. The device is described as being an artificial airway device. The device comprises a curved, flexible tube opening at one end into the interior of a hollow mask portion shaped to conform to fit readily into the actual and potential space behind the larynx and to seal around the circumference of the laryngeal inlet without penetrating into the interior of the larynx. Commercial forms of this device have an inflatable collar extending around the periphery of the mask. The inflatable collar is adapted to form the seal around the laryngeal inlet when the collar is inflated. Additionally, the mask portion included an inflatable posterior part which is adapted to press against the back of the throat and thereby increase the sealing pressure around the laryngeal inlet.

British patent no. 2,111,394 states that the shape and (when fitted) the inflatable part or parts of the mask ensure that it approximates closely to the shape of the space between the laryngeal inlet and the walls of the lower part of the throat behind it. Since the walls of tissue forming the back of the throat are relatively rigid, inflation of the mask forces it more tightly against the tissues surrounding the laryngeal inlet, so forming an airtight seal, while tending to anchor the mask in position.

In use of the device described in GB 2,111,394, the device is inserted through the mouth of the patient and down the throat past the epiglottis until the mask comes to rest with its distal end in the base of the throat, lying against the upper end of the normally closed oesophagus. The inflatable ring on the mask is then inflated to seal around the inlet to the larynx. The patient's airway is thus secure and unobstructed and the laryngeal mask can be connected directly to conventional anaesthetic circuit hosing for either positive pressure or spontaneous breathing.

When a patient is placed under general anaesthetic, the patient is frequently lying in the horizontal position on his or her back or side. When under general anaesthetic, reflex response in the body is suppressed and the sphincter closing the top of the stomach from the oesophagus is relaxed. Consequently, gastric juices (which are acidic in nature) can flow along the oesophagus. It is important to ensure that such gastric juices do not enter the trachea as aspiration of gastric juices into the lungs can have potentially fatal consequences.

Similarly, where a patient under general anaesthetic is undergoing a surgical procedure of the nose, mouth or throat (e.g. a tonsillectomy, endoscopic nasal surgery), saliva, blood and nasal secretions can travel down through the laryngo pharynx and into the trachea and thereafter into the lungs. Again, this is a potentially dangerous situation.

When using a laryngeal mask such as the one described in British patent no. 2,111,394, the present inventor has found that if significant volumes of gastric juices collect around the mask the gastric juices can work their way past the seal of the mask and into the larynx. This is dangerous if the gastric juices and acid gets into the lungs.

The laryngeal mask described in British patent no. 2,111,394 may also have problems of leakage occurring in the inflatable ring or collar, due to a faulty valve in the pilot line or due to leakage or tearing of the inflatable ring or collar. It is apparent that deflation of the cuff substantially increases the chance that the seal around the larynx will be lost, which consequently increases the possibility of gastric acids getting into the lungs. Even in normal use without cuff deflation, there remains a possibility that a gush of acid from the stomach can get around the cuff and enter the air passage as there is no other way for the acid to escape (due to the cuff totally blocking the laryngopharynx). The presently available masks also have the limitation that they cannot be used safely on all patients, especially patients with a large abdomen.

In order to minimise the likelihood of the abovementioned problems, the patentee of British patent no. 2,111,394 introduced a laryngeal mask that had a double cuff to produce a total seal around the area of the larynx. This mask also included an additional tube that extends along the back of the laryngeal mask and extends into the oesophagus. This allows gastric acid to be sucked out from the stomach by way of a Ryles tube inserted through this passage. It has been found that applying suction to the oesophageal tube of this laryngeal mask can cause the tissue of the oesophagus to be sucked into the inlet of the second tube. This results in the second tube becoming blocked, thereby preventing removal of gastric acid from the upper oesophagus.

The double cuff laryngeal mask also includes two small additional tubes that open into the larynx-side of the mask. These tubes can be used to remove from the larynx any gastric juices that make their way past the seal into the larynx. However, applying suction to these tubes raises the possibility of removing anaesthetic gases from the trachea and increases the possibility of collapsing the lung or lungs. Successful removal of all the volume of acid coming up from the stomach is also not possible. Consequently, the acid may preferably move into the large diameter airway (trachea) due to the large diameter of the airway providing a path of lower resistance to fluid flow than the smaller diameter opening in the mask and also because the trachea bronchial tube is at a lower level in a supine patient.

The improved laryngeal mask described above is described in Australian patent no. 630433.

In our International patent application no PCT/AU2004/001011, the entire contents of which are herein incorporated by cross reference, we describe a device for maintaining an airway in a patient comprising a mask, the mask having a resilient conformable peripheral portion shaped such that the mask forms a seal with the larynx when the mask is positioned in the laryngo pharynx to thereby prevent ingress of extraneous fluids into the larynx, the peripheral portion of the mask defining at least one cavity for providing fluid communication between the laryngo pharynx and the oesophagus when the mask is inserted into the laryngo pharynx, and an airway tube connected to or formed with the mask for passing gas to the larynx when the mask is properly inserted into the laryngo pharynx.

This device, in preferred embodiment, does not have an inflatable cuff around its periphery. Rather, the walls of the mask made from a resilient material and the walls themselves comprise a design in which the walls extend outwardly and then upwardly and inwardly. In this fashion, the walls assist in obtaining a seal around the larynx to prevent fluid from the oesophagus entering the larynx during anaesthesia. Further, the walls also define cavities that provide fluid communication between the laryngo pharynx and the oesophagus when the mask is inserted into the laryngo pharynx.

Although laryngeal masks such as the examples described above have found wide acceptance, difficulties can be encountered during insertion of the laryngeal mask into the airway of the patient. In particular, during insertion of the laryngeal masks, the tip of the masks has often been found to come into contact with the pharynx. This necessitates extra manipulation of the mask during insertion in order to properly position the mask in the patient.

The anatomy of the head and neck of humans includes numerous muscles, nerves and cartilages. The thyroid cartilage comprises an open and, generally semi-cylindrical cartilage that extends around the anterior of the upper part of the trachea. Located below the thyroid cartilage is the cricoid cartilage. The cricoid cartilage forms a solid ring of cartilage that extends around the upper part of the trachea. The posterior part of the cricoid cartilage is located in the wall between the trachea and the oesophagus.

The cricoid cartilage, being in the form of a solid ring or closed ring of cartilage, is used to close off the oesophagus in patients who have a possible full stomach and who require emergency surgery or who have stopped breathing. In these instances, either an endotracheal tube or a laryngeal mask is inserted into the patient in order to provide airway ventilation. However, as the patient may have a full stomach, the risk of regurgitation or vomiting is enhanced. Therefore, external cricoid pressure, in which pressure is applied externally from the anterior part of the neck to the cricoid cartilage to compress the oesophagus against the posterior pharyngeal wall, is used to include the upper oesophagus to stop regurgitated material from entering the glottic area to prevent aspiration into the lungs. The external cricoid pressure must be applied and maintained until the time that a viable airway is fully secured. It has been found, in order to successfully apply intermittent positive pressure ventilation (IPPV) using presently available laryngeal masks, external cricoid pressure is necessary. To perform an effective external cricoid pressure requires extra trained personnel.

BRIEF DESCRIPTION OF THE INVENTION

It is an object of the present invention to provide an improved laryngeal mask that overcomes or at least ameliorates one more of the above-mentioned disadvantages.

In order to clearly describe the present invention, the following conventions for determining directions will be used throughout the specification. It will be understood that, when the airway device is positioned properly in a patient, the mask will have a laryngeal side (which is the side closest to the larynx of the patient, which is also referred to as the ventral side or anterior side of the mask) and the other side, being a dorsal side, that is positioned away from the larynx. The distal end of the dorsal side faces towards the oesophagus. The proximal end of the dorsal side faces towards the oropharynx and mouth of the patient. The side of the mask that faces the larynx and when in use will be referred to throughout this specification as the "laryngeal side" or the "ventral side". In terms of directions, throughout the specification, the term "downwards" or its grammatical equivalents will referred to a direction moving towards the laryngeal or ventral side of the mask. Throughout this specification, the term "upwards" or its grammatical equivalents will referred to a direction moving towards the dorsal side of the mask.

In a first aspect, the present invention provides a device for maintaining an airway in a patient, the device comprising a mask having a peripheral portion that forms a seal with the larynx when the mask is positioned in the laryngo pharynx to thereby prevent ingress of extraneous fluids into the larynx, and an airway tube connected to or formed with the mask for passing gas to the larynx when the mask is properly inserted into the laryngo pharynx wherein the peripheral portion of the mask includes a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall.

In one embodiment, the soft, flexible portion has a part that extends inwardly, the inwardly extending portion being located at a ventral side of the mask. Suitably, the inwardly extending portion includes or defines an opening through which ventilation gases pass. Suitably, the inwardly extending soft, flexible membrane portion is caused to expand when pressurised ventilation gases are applied to the airway mask. This "inflation" pushes or urges the soft, flexible membrane into firmer contact with the tissues surrounding the laryngeal opening with greater force than is present when pressurised ventilation gases are not applied to the airway mask. As the force with which the soft, flexible membrane is pushed into contact with the tissues surrounding the laryngeal opening is increased by pressurised ventilation gases in the airway tube, the seal achieved by the soft, flexible membrane with the tissues surrounding the laryngeal opening is also improved. Thus, the strength or effectiveness of the soft, flexible membrane in achieving a seal with the tissues surrounding the laryngeal opening is proportional to the pressure of the ventilation gases supplied to the airway tube. This is in direct contrast to existing laryngeal mask airway devices in which the strength of the seal formed with the tissues surrounding the laryngeal opening is dependent upon the inflation pressure of an inflatable cuff (which inflation pressure is independent of the pressure of ventilated gases supplied via the airway tube) or dependent on the strength and resiliency of the material from which the peripheral portion of the laryngeal mask is fabricated. To improve the seal with conventional laryngeal masks, larger sized masks are also frequently used, which can cause increased patient discomfort and longer recovery time. Indeed, in presently available laryngeal masks that include an inflatable cuff to achieve a seal, when the airway pressure is increased during IPPV, the increase in the airway pressure pushes the anterior pharyngeal wall away from the already inflated and fixed peripheral cuff of the mask, which leaves a gap between the mask and the pharyngeal wall. As a result, gas can escape between the fixed inflated cuff and the pharyngeal wall.

In some embodiments, the soft flexible portion lies against and extends along the structures around the larynx when the mask is positioned in the patient, the soft flexible portion being urged or forced into contact with the structures around the larynx when pressurised gas is supplied to the mask.

The soft, flexible membrane may comprise a domed membrane, a folded membrane, or a membrane including a portion that extends substantially parallel to the tissues surrounding the laryngeal opening. The soft, flexible membrane suitably includes or defines an opening, with the soft, flexible membrane desirably having a thin wall thickness in the vicinity of the opening.

In some embodiments, the opening in the soft, flexible portion may include a ring or region of thicker material around or near the opening. This assists in maintaining the shape of the opening.

The soft, flexible membrane may be integrally formed with the mask. Alternatively, the soft, flexible membrane may be joined to the mask, for example, by use of a suitable adhesive, by ultrasonic welding, or by any other suitable joining technique.

The soft, flexible membrane may form part of a larger structure, with the larger structure having portions or regions of thicker wall thickness or less flexibility than the soft, flexible membrane. The larger structure may be arranged such that the soft, flexible membrane contacts the tissues surrounding the laryngeal opening when the airway device is inserted into a patient. The larger structure may be arranged such that the soft, flexible membrane lies against and substantially parallel to the tissues surrounding the laryngeal opening when the airway device is inserted into a patient.

The soft, flexible membrane may be utilised with any of the airway devices described in with reference to the other aspects of the present invention, as described herein.

In other embodiments of all aspects of the present invention, the mask may be made from a resilient material. When pressurised ventilation gases are supplied to the airway tube, the increased internal pressure within the mask (arising from the pressurised ventilation gases) will cause the mask to circumferentially expand. The mask may be made of varying wall thicknesses and thus its expansion can vary considerably in different parts of the mask. This expansion tends to increase the seal around the mask in all directions against the pharyngeal walls. As the part of the mask facing the anterior pharyngeal wall (i.e. the tissues surrounding the laryngeal opening) is also made with wall regions of varying thicknesses, the thinner parts expand the most and exert further pressure against the tissues that they are in contact with. This expansion of the mask is caused by the ventilation gases. Thus, the strength or effectiveness of the seal achieved by the mask is proportional to the pressure of the ventilation gases used.

In some embodiments, the device of the present invention may further include one or more loops or brackets attached to or extending from the airway tube to enable the device to be more easily taped or tied in place during use in a patient. In one embodiment, the one or more loops or brackets are positioned on a ventral side of the airway tube. In another embodiment, the one or more loops or brackets are positioned on both a ventral side and a dorsal side of the airway tube.

In yet another embodiment, the airway tube may be provided with one or more depressions to facilitate securing of the mask and for positioning of the fingers of a doctor utilising the device. For example, finger grips for two or more fingers may be formed in the airway tube.

The mask of the present invention may be used for positive pressure ventilation, for resuscitation and for use in anaesthesia.

In some embodiments, the soft flexible membrane may be provided with one or more reinforcing members, such as reinforcing ribs, to assist in maintaining the shape of the soft flexible membrane when pressurised gas is not being provided to the mask.

In some embodiments, the mask may be provided with a dorsal groove or recess near the distal tip thereof. This dorsal groove or recess tends to cause the distal tip of the mask to fold under when it contacts the posterior wall of the throat when the mask is being inserted into the patient. As insertion continues, the distal tip eventually unfolds to the correct position. Therefore, the dorsal groove or recess near the distal tip of the mask helps prevent snagging of the mask on the posterior wall of the throat during insertion. It also reduces the likelihood of damage to the mucous membranes and assists in causing the mask to move the right way during insertion into the patient.

In some embodiments, the distal end of the ventral peripheral portion of the mask includes an upwardly extending portion that extends towards the dorsal side of the mask. This is advantageous because, during insertion of the mask, as the distal end of the mask reaches the larynx, the upwardly extending portion at the distal end does not tend to enter the larynx and therefore does not tend to get stuck onto the larynx, thus lowering the risk of undesired insertion of the distal end of the mask into the larynx. In other words, the distally curved portion helps to scoop behind the larynx to make the distal end of the mask easily slide behind the larynx.

The upwardly extending portion may include one or more openings formed therein to facilitate fluid flow from the oesophagus to the proximal side of the mask during use of the mask. The upwardly extending portion may be defined by an upwardly extending wall and the opening may be in that wall.

In some embodiments of the present invention, the distal end of the mask may have a large radius of curvature. This will result in the distal end of the mask having a relatively "blunt" appearance. This is also believed to assist in facilitating insertion of the mask into the airway of a patient as the mask is less likely to snag on the structures at the back of the throat of the patient or on the inlet to the larynx.

In some embodiments, the peripheral portion of the mask may include an inflatable cuff, with the soft, flexible membrane extending from the inflatable cuff.

The distal end of the opening of the mask through which ventilation gases are supplied to the patient may be provided with a sloped region or a ramp. This sloped region or ramp allows the larynx to more easily slide over it during insertion of the mask, thereby ensuring that the larynx is properly positioned. Further, the larynx tends to become seated in the opening, thereby preventing the mask from being inserted too far into the patient and assisting in correctly positioning the mask in the patient.

The mask may be provided with one or more openings at or near its distal end, the one or more openings allowing fluid communication between the oesophagus and the throat region when the mask is inserted into a patient.

The mask may be provided with one or more longitudinally extending passageways or cavities that, in use, are in fluid communication with the oesophagus. These one or more longitudinally extending passageways or cavities may be in fluid communication with one or more openings formed in the distal tip of the mask In some embodiments, the mask of the present invention includes a central portion defining a chamber that is in fluid communication with the airway tube and, in use, in fluid communication with the larynx of a patient. A peripheral portion of the mask may be formed by the lower extremities of the chamber extending downwardly and then inwardly to thereby define a peripheral portion that, in use, forms a seal with the larynx. The peripheral portion may include the soft flexible membrane. The dorsal surface of the mask may be positioned above the chamber. The dorsal surface may include a portion that extends laterally past an upper part of the chamber. As the lower peripheral surface (or ventral peripheral surface) of the mask is formed by a downwardly extending portion and an inwardly extending portion, the lateral part of the dorsal surface and the outer edges of the peripheral portion on the ventral side of the mask may define a passageway or an opening that enables fluid communication between the oesophagus and the proximal part of the mask when the mask is in use.

In another embodiment, the mask may include a longitudinally extending wall spaced from the part of the dorsal surface that extends laterally past an upper part of the chamber. This longitudinally extending wall may define a flow passage with the part of the dorsal surface that extends laterally past an upper part of the chamber and a further flow passage with an upper part of the chamber.

In most embodiments of the present invention, the flow passages have at least one open side. It is believed that providing an open side to the flow passages allows the mask to more readily deform during insertion of the mask to thereby assist in the insertion of the mask.

In some embodiments, the mask further includes a cricoid contacting portion that extends towards the cricoid cartilage and abuts with the cricoid cartilage when the mask is properly inserted, the cricoid contacting portion being adapted to form a seal in the vicinity of the cricoid cartilage.

In some embodiments, the mask includes a distal portion that extends past the cricoid cartilage when the mask is properly inserted, The cricoid contacting portion of the mask that extends towards the cricoid cartilage may comprise a projection extending away from the inner or ventral side of the dorsal wall of the mask. This extension may extend in a ventral direction within the airway cavity or airway chamber within the mask portion. The cricoid contacting portion may be made from a resilient material so that when the portion abuts with the cricoid cartilage, it pushes the cricoid cartilage away from the posterior pharyngeal wall. This may create an actual space between the cricoid cartilage and the posterior pharyngeal wall. In some embodiments, the cricoid contacting portion of the mask may exert pressure against the posterior and the posterolateral sides of the cricoid cartilage. This acts to open the crico-pharynx and the upper end of the oesophagus to allow a free flow of fluid from the oesophagus to the rest of the pharynx and this, in turn, may allow any fluid regurgitated from the stomach to be cleared by suction.

Additionally, the cricoid contacting portion of the mask that abuts with the cricoid cartilage forms an improved seal between the cricoid contacting portion of the mask and the cricoid cartilage, thereby improving the seal around the larynx that can be attained using the mask. Further, the cricoid contacting portion also ensures that the upper oesophagus is placed in and remains in good fluid communication with the sump area and the passageways in the mask. The sump area is formed by the passageways in the side of the mask portion, the opening in the distal end of the mask and by any transversely extending openings in the mask that allow fluid communication between the passageways.

The cricoid contacting portion that extends towards the cricoid cartilage may be shaped such that the posterior portion of the cricoid cartilage snugly fits into the cricoid contacting portion. The cricoid contacting portion also forms an improved seal in the vicinity of the cricoid cartilage.

The cricoid contacting portion may have a resilient and conformable surface that, in use, abuts with the cricoid cartilage. This allows the surface that abuts with the cricoid cartilage to form a very good seal in the vicinity of the cricoid cartilage.

The cricoid contacting portion may be in the form of a sling into which the cricoid cartilage snugly fits.

The region of the mask portion positioned dorsally of the cricoid contacting portion may act like a bridge. The bridge may have one or more openings therein (which may be transverse openings) which provide fluid communication laterally between the passageway on one side of the mask portion and the passageway on the other side of the mask portion. This opening or openings allows any regurgitated fluid to travel between the passageways on either side of the mask and also form a large sump area for collecting regurgitated fluid. Further, by applying suction to only one of the passageways, fluid can be removed via that passageway. Venting air can travel up the other passageway so that the formation of a negative pressure zone in the sump area is avoided. The openings in the bridge allow proper fluid communication between the passageway that has suction applied to it and the passageway that allows venting air to flow along it, so that venting air can readily flow up the passageway, through the openings (and thus flow laterally across the mask) and then down the passageway that has suction applied to it.

The mask portion may also define a sump area. The sump area may be defined by the passageways, and the transverse openings through the mask. The opening or openings at the distal end of the mask also form part of the sump region or sump area.

The cricoid contacting portion technically forms a new concept of posterior cricoid pressure which enables the fluid from the oesophagus to flow easily, enabling that fluid to be quickly cleared from the sump area by applying high suction to one of the passageways in the mask, or at least to allow regurgitated fluid to easily flow out of the upper oesophagus, which assists in preventing a build up of fluid under pressure in the upper oesophagus, which can be potentially dangerous for causing aspiration of fluid into the lungs of the patient.

The mask may have a chamber having an inner wall, the chamber facing towards the larynx during use of the mask. The peripheral portion of the mask suitably extends around the chamber. The peripheral portion of the mask is suitably formed as an extension of the ventral part of the chamber. The chamber is in fluid communication with the airway tube such that gases can be delivered from the airway tube into the chamber and thereafter into the larynx and trachea of the patient. The cricoid contacting portion may extend away from a dorsal inner wall of the chamber. Alternatively, the cricoid contacting portion may comprise a projection or elevation that is ventrally located relative to the dorsal inner wall of the chamber.

The cricoid contacting portion may be located towards the distal end of the mask.

The distal end of the mask may include a region that extends towards the dorsal side of the mask. This region may comprise a ramp or sloped region that extends towards the dorsal side of the mask. This region may comprise a distal extension of the cricoid contacting portion.

In some embodiments, the cricoid contacting portion applies pressure to the cricoid cartilage using a spring action effect from within the mask. This helps to achieve a complete seal around the larynx which, in turn, allows a higher IPPV pressure and prevent aspiration of fluid regurgitated from the stomach. This isolates the air passage or trachea from the oesophagus but allows the oesophagus to be drained in the event that fluid from the stomach travels up the oesophagus.

In some embodiments, the device may include ventral curvature at the proximal portion of the mask, or near where the mask and airway tube joint or merge. It is believed that this assists in inserting the mask into the patient. In some embodiments, the mask may further include curvature in the opposite direction in a region of the airway tube that is proximal to the ventral curvature. This helps to push the tip of the mask dorsally during insertion, which assists in forwarding or minimising the likelihood of snagging of the mask on the larynx during insertion. Providing a dorsally extending ramp at or near the distal end of the mask also assists in this regard.

In some embodiments, a soft flexible membrane may be shaped such that it extends into and fills the piriform recess when the mask is supplied with ventilation gas. The piriform recess is a structure near the entrance to the larynx. This structure provides a soft area on either side of the larynx that does not have underlying bone or cartilage supporting it. Therefore, the piriform recess is a site for potential leaks when the mask is inserted into the patient in currently available laryngeal masks. By providing the soft flexible membrane, the ventilation gases can cause the soft flexible membrane to bulge into the piriform recess, entrapping the ventilation gases and to therefore provide an enhanced seal in the region of the piriform recess.

In some embodiments, the device may be used to facilitate intubation of a patient. In such embodiments, the dorsal wall of the mask portion may include a ventral extension which acts as a ramp or a guide to guide an end of an endotracheal tube being inserted through the mask through the opening of the mask and into the trachea of the patient. In one embodiment, the ventral extension may form an additional extension extending from the cricoid contacting portion of the mask. Alternatively, the ventral extension may comprise a separate structure just proximal to the cricoid contacting portion extending across the under surface of the dorsal wall within the airway chamber.

In other embodiments, the device may include a barrier extending upwardly into the chamber of the mask portion, the barrier forming a guide to guide an end of an endotracheal tube being inserted through the mask through the opening and into the trachea of a patient.

In one embodiment, the barrier comprises a flap. The flap may have a free end or a free edge. The flap may have a tapering width as it extends in an upwardly direction. In another embodiment, the barrier comprises a wall portion extending upwardly from a distal end of the opening in the mask towards the dorsal side of the mask.

In one embodiment, the flap extends upwardly from around a distal portion of the opening.

In one embodiment, the dorsal wall of the mask portion is shaped to receive the flap. For example, the dorsal wall may include a recess formed in the dorsal wall of the chamber, said recess receiving the flap. Alternatively, where the dorsal wall includes a ventral extension that is separate to the cricoid contacting portion, the ventral extension may extend ventrally from the inner dorsal wall from a position proximal to the cricoid contacting portion, the ventral extension including a distal portion that extends dorsally, and the cricoid contacting portion extending ventrally from the distal portion of the ventral extension. In this embodiment, the distal end of the ventral extension defines a recess positioned distally of the ventral extension, which recess can receive the barrier or flap.

In one embodiment, the barrier or flap moves into the recess when the device is inserted into a patient. In this regard, inserting the device into the patient may deform the peripheral portion of the device (by virtue of the interaction between the peripheral portion of the device and the tissues of the patient), said deforming causing the flap to move so that it extends into the recess. In some embodiments, the flap may lie against a wall of the recess, or the flap may lie against the cricoid contacting portion. In this embodiment, the flap presents a surface to an endotracheal tube, and therefore causes the end of the endotracheal tube to move along the flap and out through the opening in the device as the endotracheal tube is inserted.

The recess may have a proximal end wall that extends below an upper end of the flap when the flap is extending into or lying in the recess. In this manner, a free end of the flap cannot come into contact with the end of the endotracheal tube as the endotracheal tube will contact the proximal end wall of the recess and slide below the free end of the flap as the endotracheal tube is inserted. Suitably, the proximal end of the dorsal wall includes a portion that extends towards the ventral side of the mask, with the dorsal wall extending upwardly at the proximal end of the recess, the recess including a downwardly extending distal portion.

The mask of these embodiments are particularly suitable for intubating a patient or for inserting other equipment into the trachea of the patient.

In some embodiments, the soft flexible portion has a thickness of between 0.1 mm to 1 mm, more suitable from 0.1 mm to 0.6 mm. The soft flexible portion will generally have a thinner wall thickness than other parts of the mask.

The mask may be made from any suitable polymeric material, such as elastic polymers, medical grade polymers or food grade polymers, including silicone polymers, PVC, nitriles, urethanes, etc. The person skilled in the art will readily understand that a number of materials are suitable for use in manufacturing the device of the present invention.

In a further embodiment, the present invention provides a laryngeal mask having a mask portion and an airway tube, the mask portion having a periphery that forms a seal with the structures around a larynx of a patient, the mask portion including an opening in fluid communication with the airway tube, an inner dorsal wall of the mask portion including a ventrally extending region which acts as a ramp or a guide to guide an end of an endotracheal tube being inserted through the mask through the opening of the mask and into the trachea of the patient. The laryngeal mask may include a barrier extending upwardly into the chamber of the mask portion, the barrier forming a guide to guide an end of an endotracheal tube being inserted through the mask through the opening and into the trachea of a patient.

In another aspect, the present invention provides a device for maintaining an airway in a patient, the device comprising a mask, the mask having a peripheral portion that forms a seal with the larynx when the mask is positioned in the laryngo pharynx to thereby prevent ingress of extraneous fluids into the larynx, an airway tube connected to or formed with the mask for passing gas to the larynx when the mask is properly inserted into the laryngo pharynx, the mask having a cricoid contacting portion that extends towards the cricoid cartilage and abuts with the cricoid cartilage when the mask is properly inserted, the cricoid contacting portion being adapted to form a seal in the vicinity of the cricoid cartilage.

In order to further understand the present invention, preferred embodiment of the present invention will now be described with reference to the accompanying drawings.

BRIEF DESCRIPTION OF THE DRAWINGS

FIG. 2 shows a perspective view from a different side of the laryngeal mask shown in FIG. 1;

FIG. 3 shows an end view of the laryngeal mask shown in FIG. 1;

FIG. 7 shows an end cross sectional view taken along cross section line E-E shown in FIG. 6;

FIG. 8 shows an end cross-sectional view taken along cross-section line F-F shown in FIG. 1;

FIG. 10 shows a front view of the mask shown in FIG. 9;

FIG. 11 shows a cross-sectional side view taken along Section line A-A shown in FIG. 9;

FIG. 16 shows a front view of the mask shown in FIG. 15;

FIG. 17 shows a cross-sectional side view taken along Section line A-A shown in FIG. 16;

FIGS. 37A and 37B are cross sectional side views of the laryngeal mask shown in FIG. 35;

FIG. 38A to 38D show front cross-sectional views taken along lines B-B to E-E, respectively (as shown in FIG. 38) of the laryngeal mask shown in FIG. 35;

FIG. 39B shows a top cross-sectional view (as taken along line F-F in FIG. 39) of the laryngeal mask shown in FIG. 35;

Figure 43:
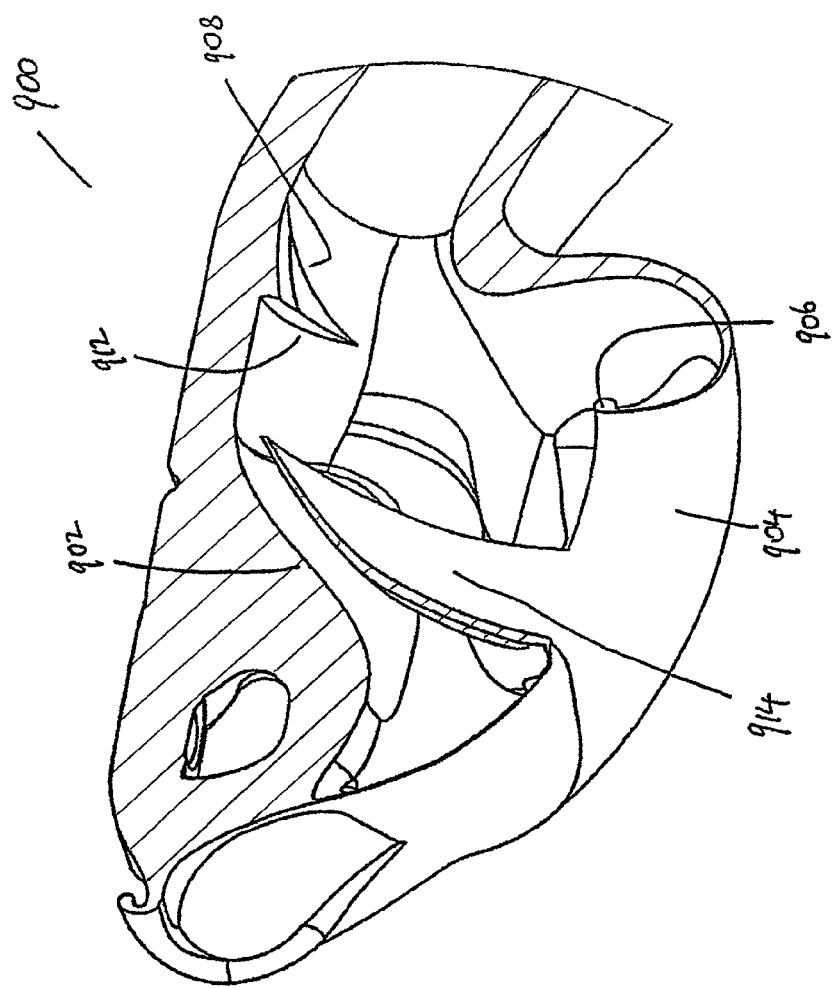
FIG. 43 shows a cross sectional perspective view of a laryngeal mask in accordance with another embodiment of the present invention.
Figure 44:
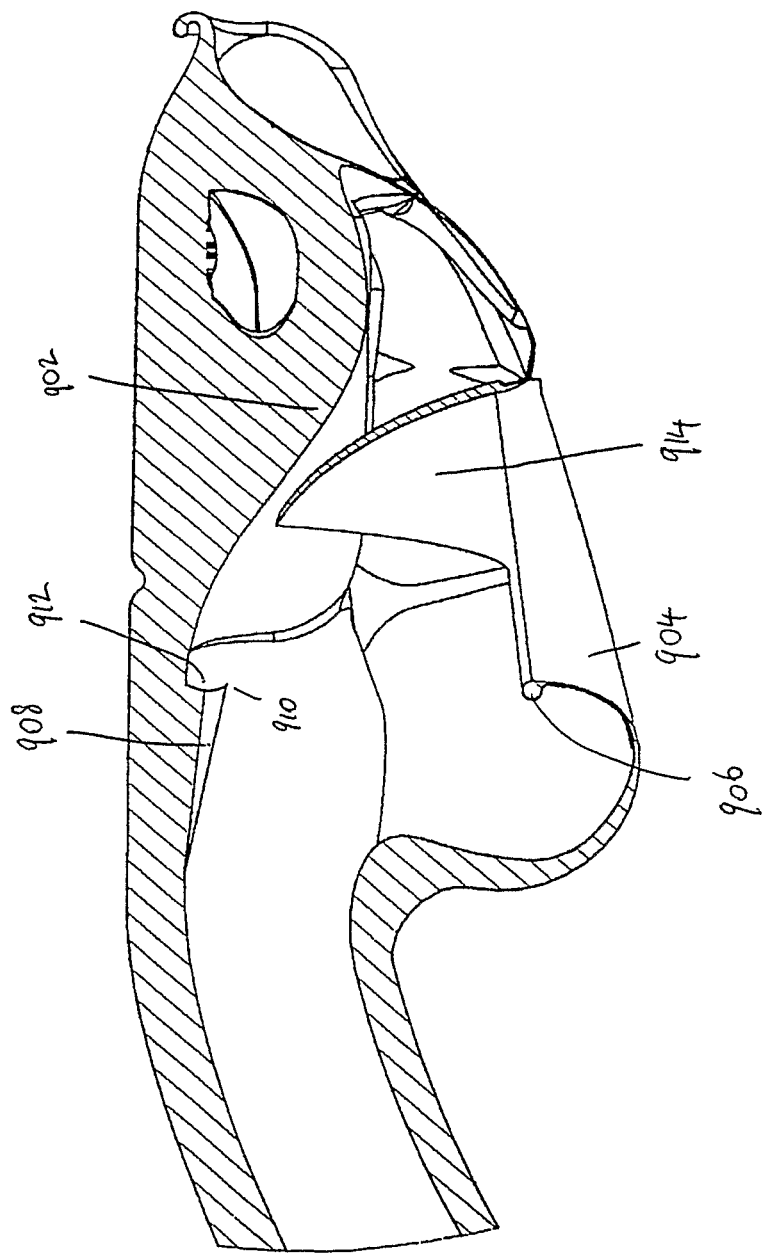
Figure 45:
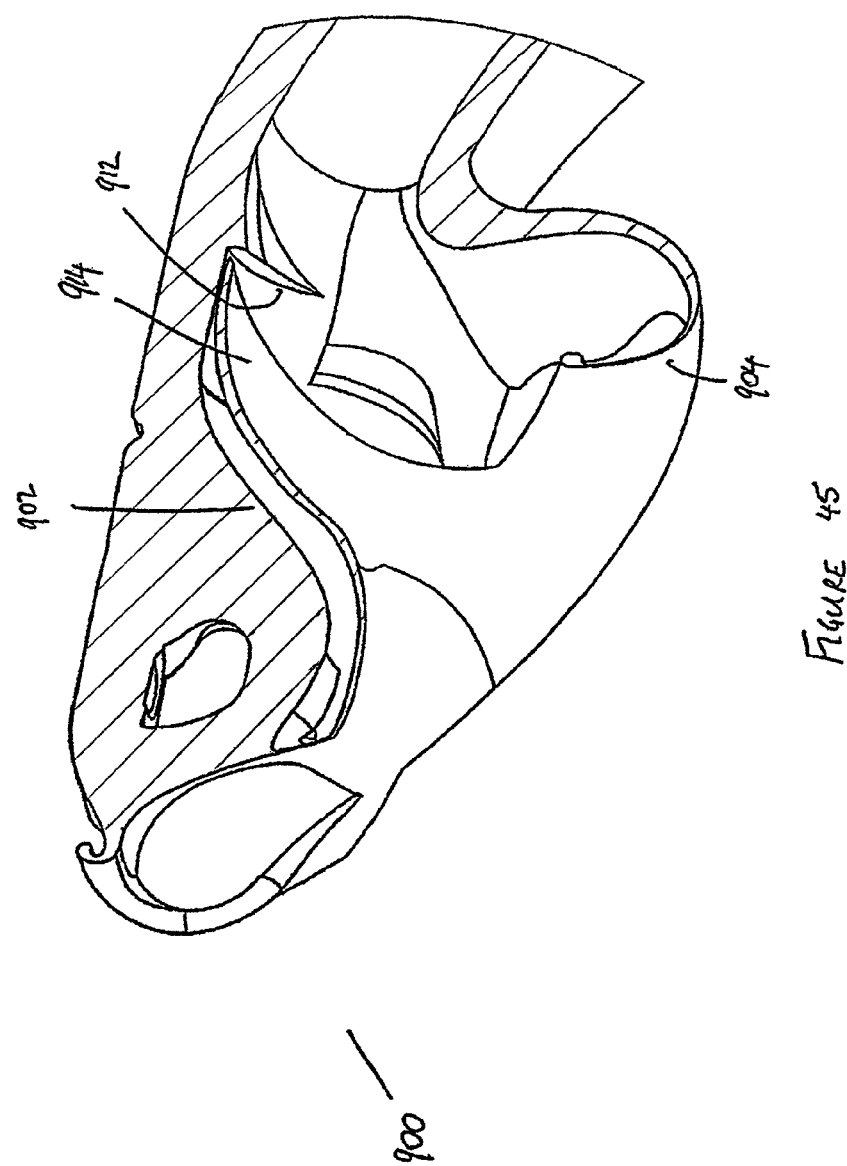
Figure 46:
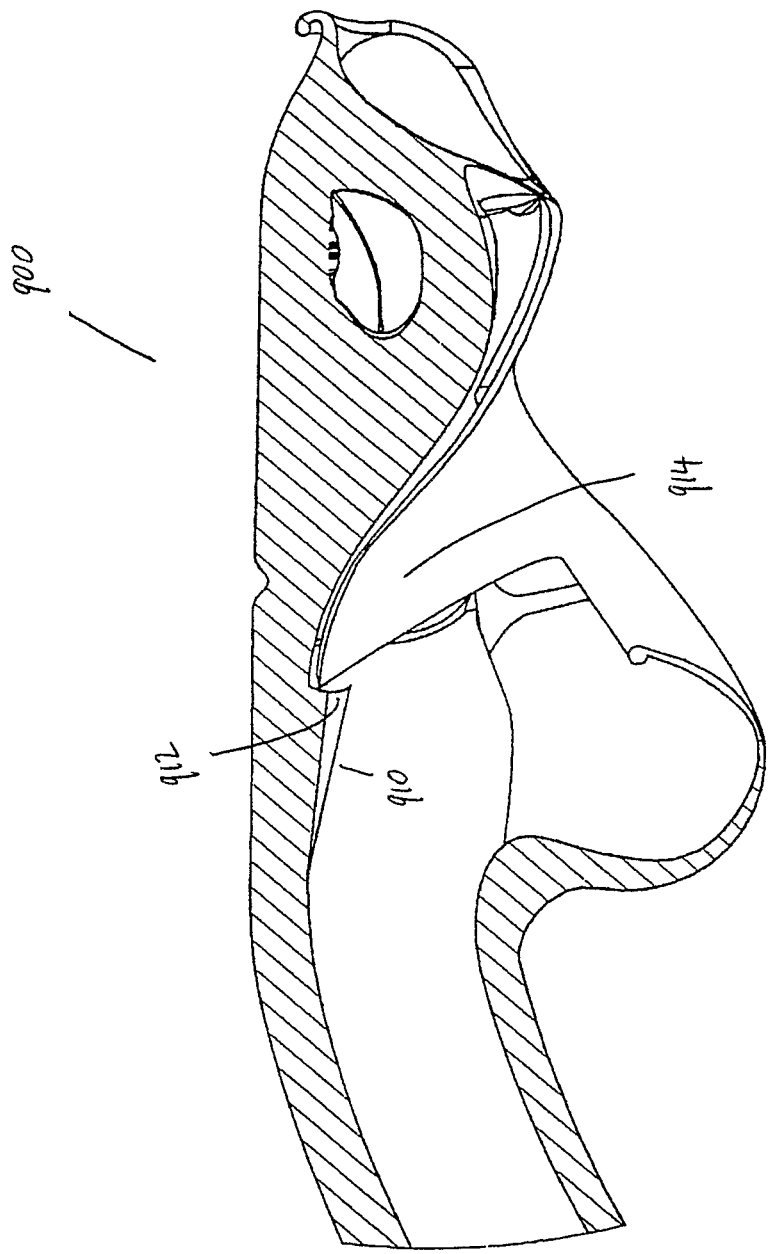
Figure 47:
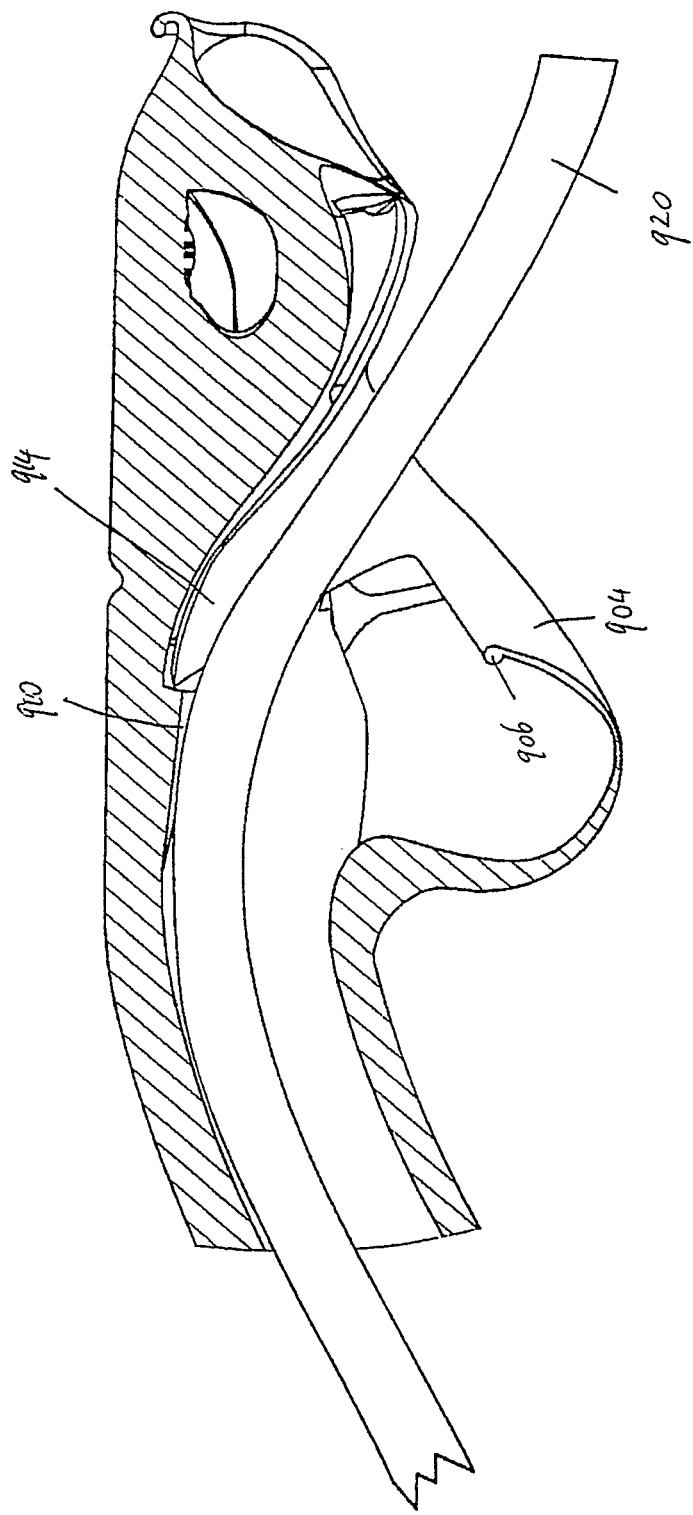

FIG. of 44 shows a cross sectional side view of the laryngeal mask shown in FIG. 43;

FIG. 45 shows a cross sectional side view of the laryngeal mask shown in FIG. 43, with a barrier member located adjacent to the inner dorsal wall;

FIG. 46 shows a cross sectional side view of the laryngeal mask shown in FIG. 45; and FIG. 47 shows a cross sectional side view of the laryngeal Ma shown in FIG. 46 with an endotracheal tube or an optical fibre light guide passed through the mask.

DETAILED DESCRIPTION OF THE DRAWINGS

It will be appreciated that the drawings have been provided for the purposes of illustrating preferred embodiments of the present invention. Thus, it will be understood that the present invention should not be considered to be limited solely to the features as shown in the accompanying drawings.

The laryngeal mask 100 shown in FIGS. 1 to 8 comprises a mask portion 102 and an airway tube 104. The mask portion 102 and the airway tube 104 may be integrally formed together or they may be formed as separate pieces that are subsequently fitted or joined together.

Figure 6:
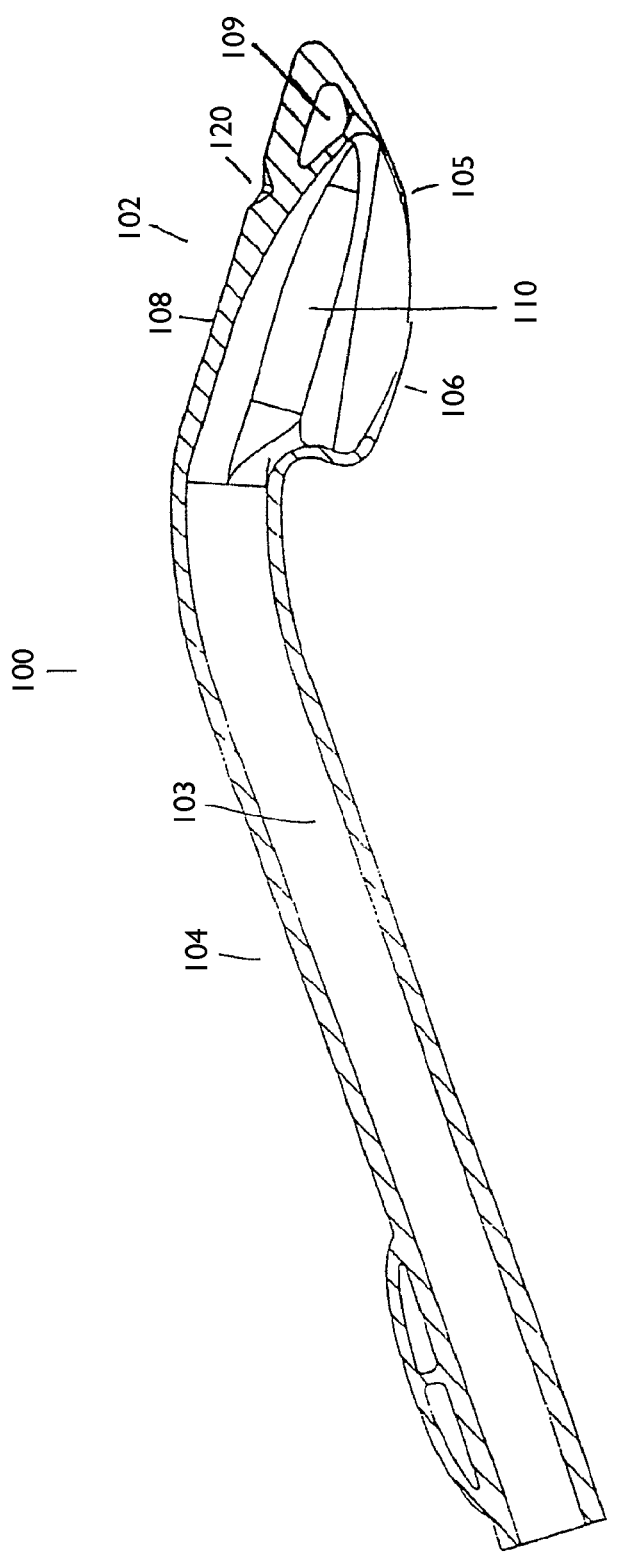
FIG. 6 shows a longitudinal cross sectional view of the laryngeal mask shown in FIG. 1.

The mask portion 102 includes a periphery 105 that, in use, extends around and forms a seal with the larynx of the patient. The mask portion 105 also includes a roof 108 that defines an upper portion or a dorsal portion of the mask 102. As shown in FIG. 6, a chamber 110 is defined in the mask 102. The chamber 110 is in fluid communication with the air flow tube 103 in airway tube 104. This can also be clearly seen in FIG. 6.

The airway tube 104 includes brackets or tags 112 that allow the airway tube to be tied or taped into position. The laryngeal mask is also provided with finger grips 114 that allow for ease of use.

The laryngeal mask 100 also includes passageways 116, 118 that extend from the distal portion of the mask towards the proximal portion of the mask. These passageways allow regurgitated material from the stomach to move past the mask and to be removed from the patient by use of an appropriate suction tube. In some embodiments, suction may be applied to one of the passageways 116, 118 to remove regurgitated materials and venting air may be allowed to pass up the other of the passageways. These passageways are formed partly by the shape of the peripheral portion 105 of the mask 102 and partly by the overhanging roof portion of the mask portion 102. It will be understood that, in use, the passageways 116, 118 provide a flow path for fluids regurgitated from the oesophagus. These passageways form a sump area at or near the distal end of the mask portion 102 and material, such as blood or fluids, may be removed from the sump area. A transversely extending opening 109 may extend between passageway 116 and passageway 118 to allow fluid communication between the passageways.

The mask portion 102 includes a soft, flexible membrane 106. This soft, flexible membrane 106 is positioned on the ventral side of the mask portion 102. The membrane 106 has an opening 109A formed therein. The opening 109A is in fluid communication with the internal chamber of the mask portion 102 which, in turn, is in fluid communication with the airway tube. Therefore, ventilation gases to be supplied to the patient travel through the airway tube into the internal chamber of the mask portion 102 and then through the opening 109A into the *trachea* of the patient.

The soft flexible membrane 106 includes a ventral wall portion 111 that extends around the vicinity of opening 109A. The ventral wall portion 111 is shaped and positioned such that when the mask is inserted into a patient, the ventral wall portion 111 lies generally parallel to the tissues surrounding the laryngeal inlet. Further, as best shown in FIGS. 7 and 8, the soft flexible membrane 106 extends ventrally from regions 112A and 114A which partly define the passageways 116, 118 that enable removal of gastric material that may be regurgitated by the patient. In particular, the wall sections 112A, 114A extend outwardly and then turn inwardly into the soft flexible membrane 106, with the soft flexible membrane 106 being located ventrally of wall sections 112A, 114A. As can also be seen from FIGS. 6, 7 and 8, the ventral wall portion 111 of the soft flexible membrane 106 has a thinner wall section than the wall sections 112A, 114A.

FIGS. 7 and 8 also show the airway passage 103 that supplies ventilation gases to the patient.

Due to the shape of the ventral portion of the mask, when pressurised ventilation gases are supplied to a patient (for example, as occurs on an intermittent basis during positive pressure ventilation), the pressurised gases exert forces on the walls of the mask as shown by the arrows in FIG. 7. The ventilation gases also pass out through the opening 109A. Due to the forces applied by the ventilation gases, the soft, flexible membrane 106 is pushed outwardly by the ventilation gases. This results in the soft flexible membrane 106 being pushed into better contact with the underlying tissues, thereby effecting a better seal between the soft flexible membrane 106 and the underlying tissues. As a result, increasing the pressure of the ventilation gases results in an enhanced seal between the soft flexible membrane 106 and the underlying tissues, with the result that the likelihood of leakage is minimised. Indeed, the present inventor believes that using the apparatus as shown in FIGS. 1 to 8 can result in formation of a seal that can withstand an internal pressure within the chamber of the mask of over 60 cm $H_2O$. In contrast, currently available laryngeal masks can only withstand internal pressures of between 20 to 45 cm $H_2O$.

In FIGS. 6 and 7, it can be seen that the membrane portion 106 extend outwardly from the opening 109A and an upwardly towards the dorsal side of the mask. When the mask shown in FIGS. 7 and 8 is inserted into the patient, the structures of the larynx essentially abut with and lie below (in the direction as shown in FIG. 7) in the outwardly extending part of the membrane portion 106 that extends outwardly from the opening 109. Thus, it can be seen that the shape of the membrane portion "captures" effectively the applied air supplied via the airway tube to thereby enhance the seal. Further, the risk of the applied air pressure blowing past or blowing out the membrane is minimised.

The mask 100 also includes a notch or depression 120 that allows for bending therearound, which facilitates insertion of the mask. In some embodiments, the notch or depression 120 may be omitted and the mask may be provided with an angle or slope at the end of the mask on the dorsal aspect of the tip to enable the tip to turn downwardly in the airway to enable the mask to bend towards the larynx during insertion.

Figure 4:
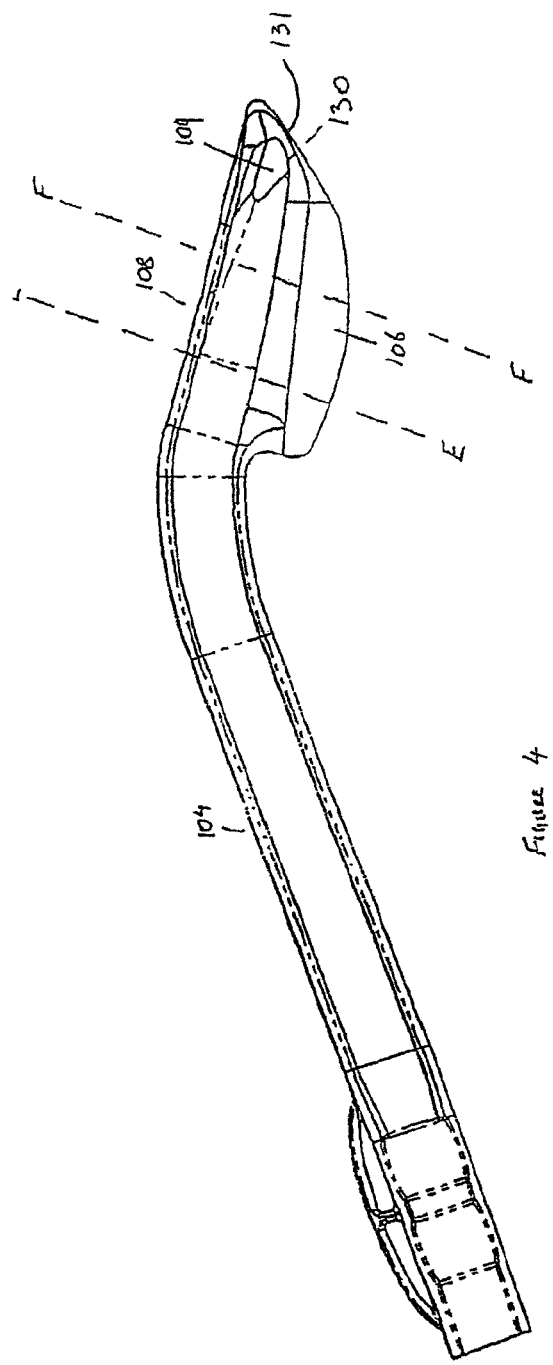
FIG. 4 shows a side view of the laryngeal mask shown in FIG. 1.
Figure 5:
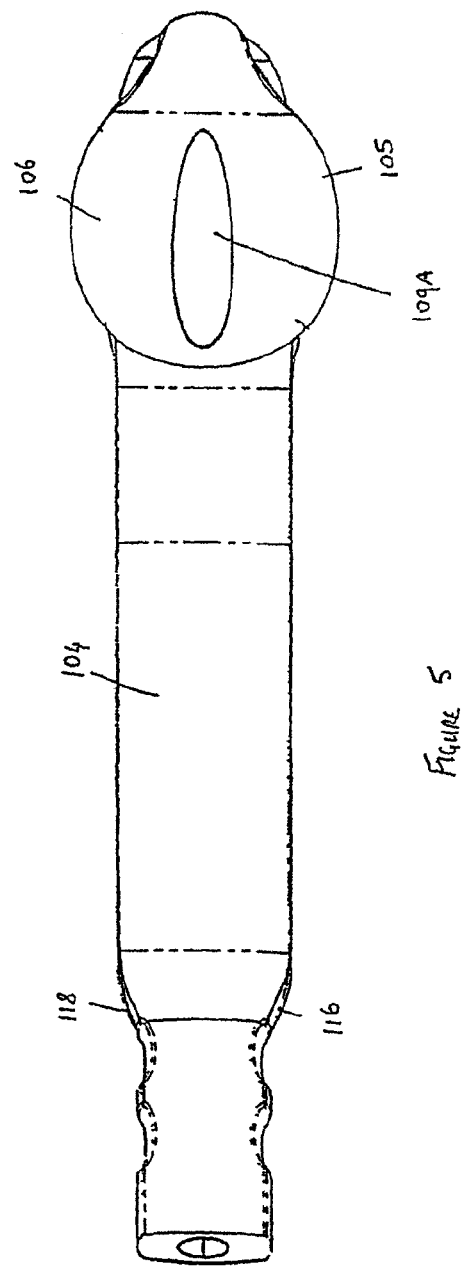
FIG. 5 shows a bottom view of the laryngeal mask shown in FIG. 1.

The distal end 130 of the mask portion 102 comprises an upwardly extending end. This is best shown in FIG. 4. The upward extension of distal end 130 of the ventral portion of the mask portion 102 forms a sloped region or a ramp 131 that assists in minimising the likelihood of the mask becoming snagged on the larynx or entering the larynx during insertion of the mask and also facilitates the distal end of the mask to easily slide behind the larynx. This portion of the mask may act as a ramp.

FIGS. 9 to 14 shown various views of another embodiment of the present invention. The device 200 shown in FIGS. 9 to 14 includes a mask portion 202 and an airway tube 204. Indeed, the device shown in FIGS. 9 to 14 includes a number of features that are common with the device shown in FIGS. 1 to 8. For convenience and brevity of description, the features of the device shown in FIGS. 9 to 14 that are common with the features shown in FIGS. 1 to 8 will be denoted by similar reference numerals in FIGS. 9 to 14, with the exception that the leading "1" in the reference numerals used in FIGS. 1 to 8 will be replaced with a leading "2" in the reference numerals used in FIGS. 9 to 14. These features need not be described further.

Figure 9:
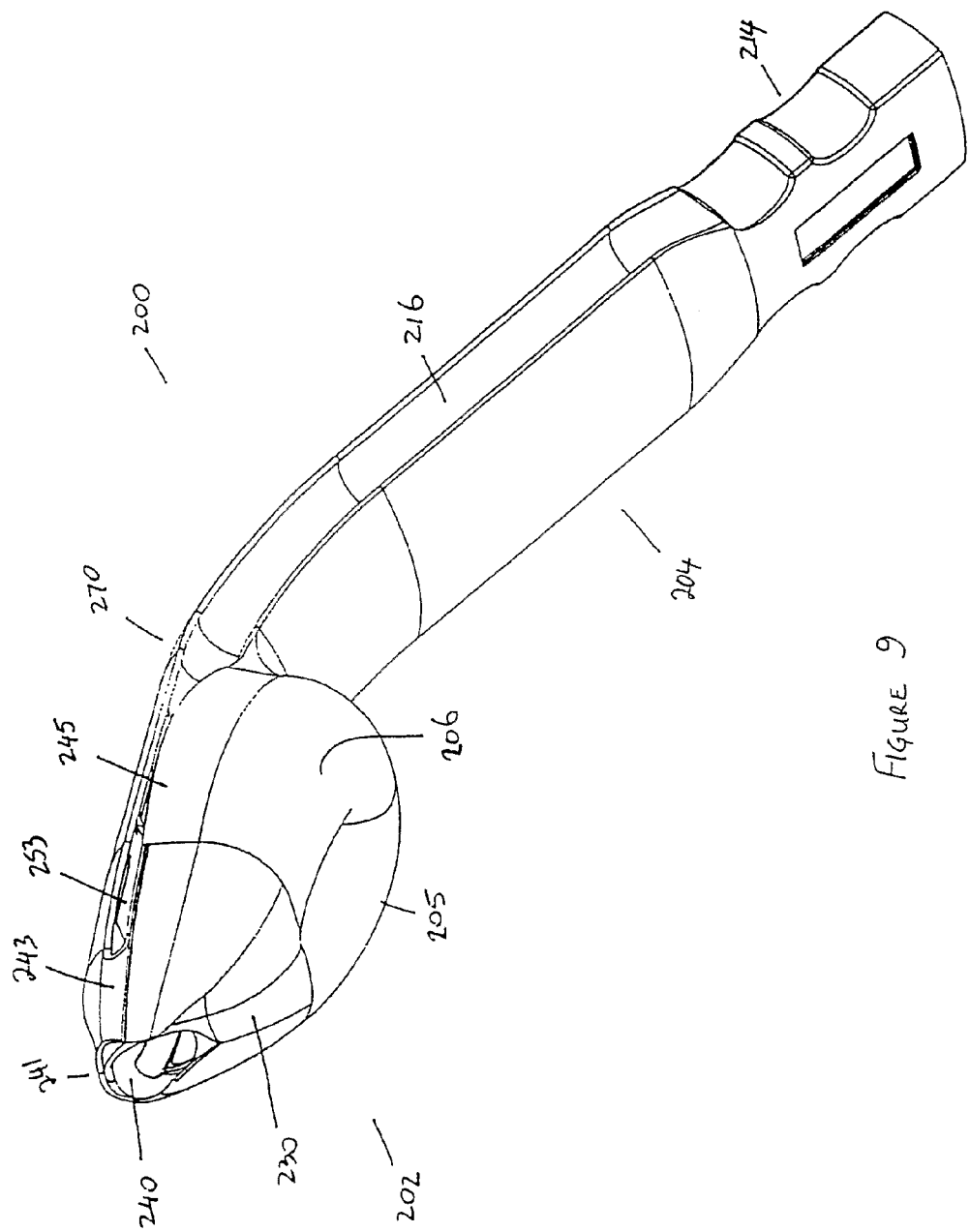
FIG. 9 shows a perspective view of a laryngeal mask in accordance with another embodiment of the present invention.

As shown in FIG. 9, the soft flexible region 206 comprises an inner wall 290 that extends in the dorsal direction from the ventral-most part of the soft flexible region 206. The dorsal end 292 of the inner wall 290 defines the opening from the airway chamber through which the ventilation gases or anaesthetic gases exit the mask portion and pass into the larynx of the patient.

The mask portion 202 includes the soft flexible membrane 206. Additionally, the distal end of the mask portion 202 includes an opening 240 that is in fluid communication with the passageways 216, 218. The end portion of the mask 241 that surrounds the opening 240 is flexible and is designed to bend as the mask is inserted and comes into contact with the posterior wall of the throat. As the mask is a further inserted, the resiliency of end portion 241 causes the end portion 241 to fold back to its correct orientation. This facilitates insertion of the mask into the patient. Furthermore, the mask shown in FIG. 9 further includes a closed wall 243 near the opening 240. Although not shown in FIG. 9, a similar closed wall is provided on the other side of opening 240. Closed wall 243 acts as a strengthening or reinforcing part for the distal tip of the mask. The present inventor has found that the strengthening or reinforcing part 243 assists in stopping the mask from folding over at the distal end during insertion into a patient. With some masks, during insertion, the tip of the mask tends to enter the piriform recess more often than travelling straight under the larynx. This tends to cause the mask to get caught at the sides of the larynx at the piriform recess and then to fold over upon itself, causing obstruction. However, the strengthening or reinforcing part 243 stops the tip of the mask from folding over. Inclusion of the strengthening or reinforcing part 243 into the mask prevents the mask from folding over itself as it passes the piriform recess during insertion. Further pushing of the mask results in the mask being properly inserted, with the larynx being properly positioned. As can also be seen in FIG. 9, the peripheral side walls 245 of the peripheral portion 206 also extend upwardly towards the dorsal region to a larger extent then for the mask shown in FIG. 1. This also assists in preventing the mask from folding over upon itself during insertion.

Turning now to FIG. 11, of particular note in the laryngeal mask 200 is the cricoid contacting portion 250. The cricoid contacting portion 250 is formed as a raised region or elevation extending from the dorsal wall 252 of air chamber 254. In particular, the dorsal wall 252 of the chamber 254 includes a ventral extension 256 that leads into the cricoid contacting portion 250.

The cricoid contacting portion 250 may also include transversely extending openings 253, 255. As best shown in FIG. 9, these openings 253, 255 are located externally to the air chamber 254 (FIG. 9 only shows opening 253). Thus, openings 253, 255 allow fluid communication between passageway 216 and passageway 218 that are located on either side of the mask. A support column 257 extends between openings 253 and 255 (see FIG. 11) and this also assists in maintaining the shape of the cricoid contacting portion 250 during use. Openings 253 and 255 allow for venting air to flow transversely across the mask and thereby avoid or minimise the creation of a region of negative pressure that might otherwise be formed if suction is applied to one of the passageways 216 or 218.

The cricoid contacting portion 250 is suitably made from a resilient, conformable material that can closely conform to the shape of the cricoid cartilage when the mask is properly inserted in the patient. In this regard, the cricoid contacting portion 250 may be made from a soft, conformable surgical grade polymer or elastomer, or even from a surgical grade silicone rubber. The cricoid contacting portion 250 is suitably arranged such that it forms a good seal in the vicinity of the cricoid cartilage and also acts to apply pressure to the cricoid cartilage (which, in turn, assist in maintaining the seal). By applying pressure to the cricoid cartilage, the cricoid contacting portion 250 also acts to maintain the upper part of the oesophagus open, to thereby facilitate removal of regurgitated material therefrom.

Figure 12:
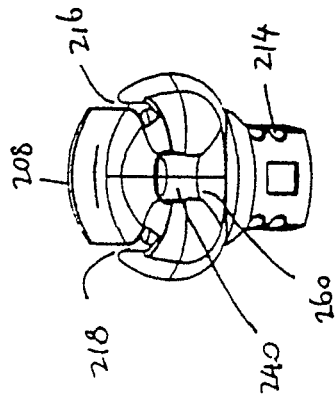
FIG. 12 shows an end view of the laryngeal mask shown in FIG. 9.
Figure 13:
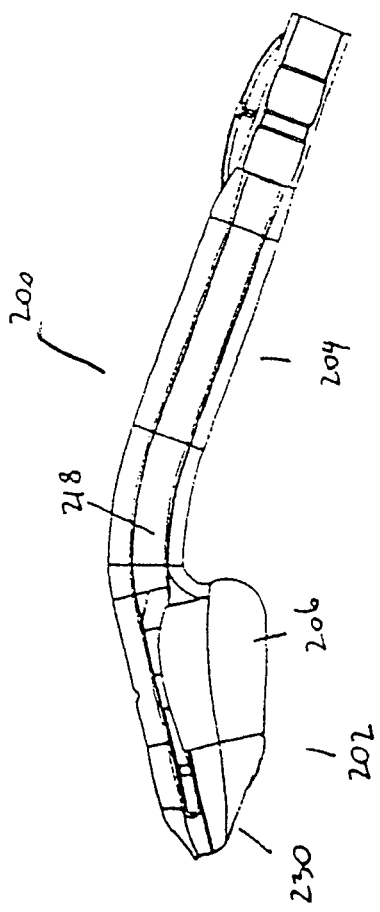
FIG. 13 shows a side view of the laryngeal mask shown in FIG. 9.
Figure 14:
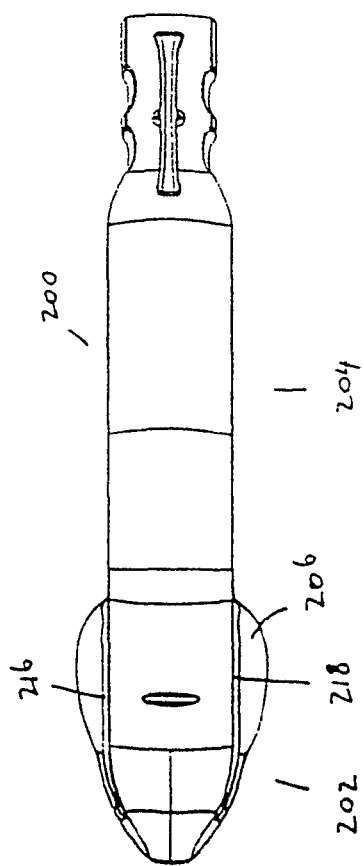
FIG. 14 shows a top view of the laryngeal mask shown in FIG. 9.

Turning now to FIG. 12, it can be seen that the ventral distal end of the mask portion 202 includes a sling shaped region 260. This sling shaped region 260 also forms part of the cricoid contacting portion 250. The shape of the sling shaped region 260 assists in creating the internal or posterior cricoid pressure and in maintaining a seal between the mask and the tissues of the patient in the vicinity of the cricoid cartilage.

The laryngeal mask 200 also includes a proximal curvature 270 which is located near a proximal region of the mask portion 202.

The mask portion 202 laryngeal mask 200 shown in FIGS. 9 to 14, when compared to existing laryngeal masks, is somewhat shorter in the length. For example, the mask portion 202 may have a length that is only about two thirds the length of currently commercially available laryngeal masks. This assists in facilitating insertion of the mask into the patient.

Figure 9A:
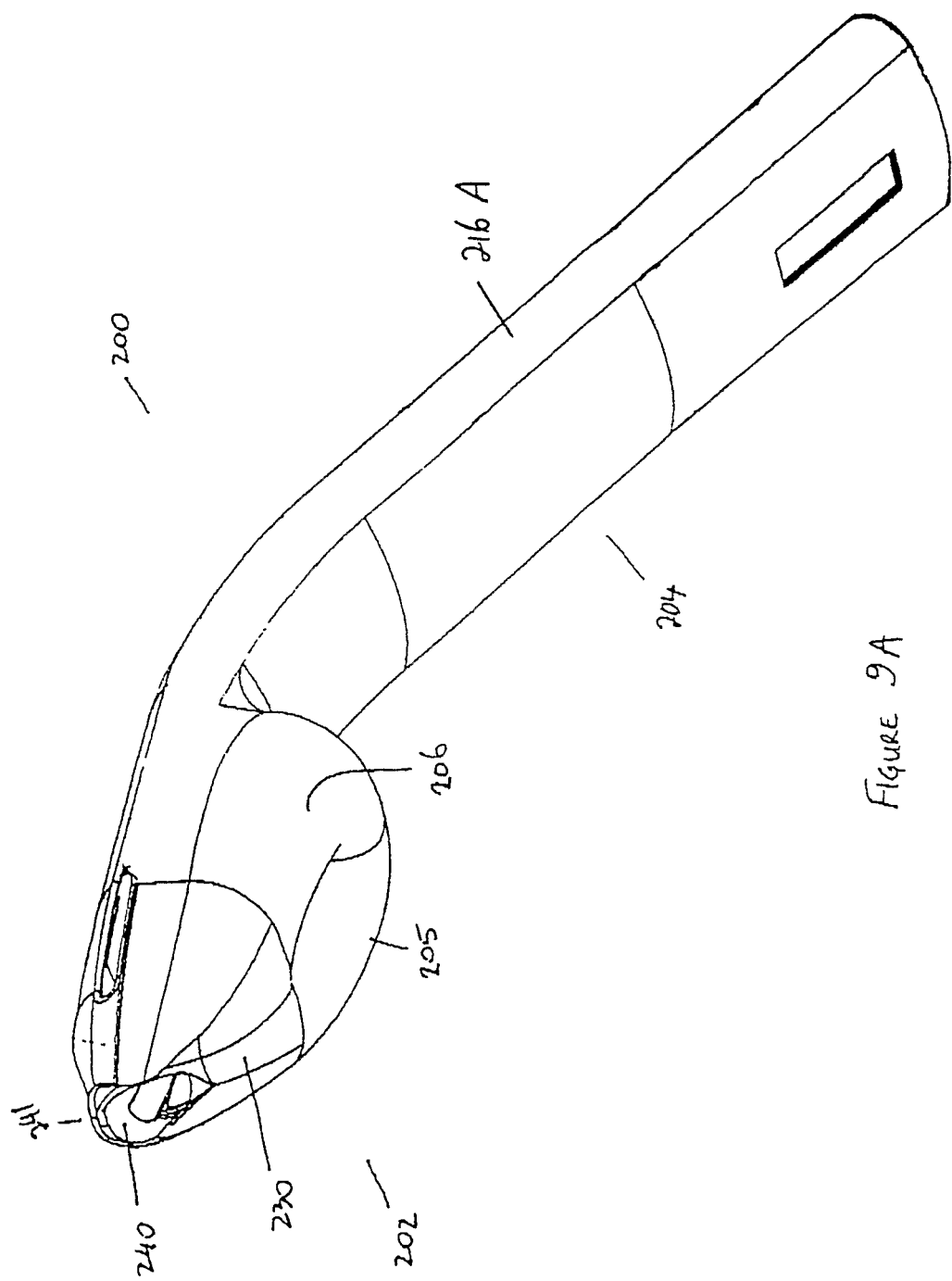
FIG. 9A shows a perspective view of a mask that is generally similar to the mask shown in FIG. 9.

FIG. 9A shows a perspective view of a mask that is generally similar to that shown in FIG. 9 and, for convenience, like features have been denoted by the same reference numerals as used in FIG. 9 but with the addition of a '. Where the mask of FIG. 9A differs from that shown in FIG. 9 is that the open passageways 216 of the mask of FIG. 9 have been replaced by closed walls 216A. Therefore, the closed walls effectively make tubes extending along the lateral edges of the mask and airway tube.

FIGS. 15 to 20 shown a laryngeal mask 300 that has many features in common with the mask 200 shown in FIGS. 9 to 14. Indeed, the device shown in FIGS. 15 to 20 includes a number of features that are common with the device shown in FIGS. 9 to 14. For convenience and brevity of description, the features of the device shown in FIGS. 15 to 20 that are common with the features shown in FIGS. 9 to 14 will be denoted by similar reference numerals in FIGS. 15 to 20, with the exception that the leading "2" in the reference numerals used in FIGS. 9 to 14 will be replaced with a leading "3" in the reference numerals used in FIGS. 15 to 20. These features need not be described further.

The main difference between the mask shown in FIGS. 9 to 14 and the mask shown in FIGS. 15 to 20 is that the mask 300 shown in FIGS. 16 to 20 includes a distal extension 365 extending forwardly from opening 340 and is in fluid communication with the passageways 316, 318. The distal extension 365 acts as a flexible, membranous funnel which, when in the correct inserted position in a patient, will open into and cover off the inner circumference of the upper oesophagus to capture any regurgitated fluid from the oesophagus and direct it towards the distal openings. This further minimises the risk of regurgitated fluid being aspirated into the lungs. In some embodiments, the distal extension 365 may have a concertina like formation. The present inventor has found that the size of the cross sectional area of the oesophagus, when dilated by upcoming regurgitated fluid, can vary from person to person. The flexible funnel like structure 365 allows for compensation for the extra cross sectional area of a dilated oesophagus to assist in containing the regurgitated fluid within its lumen so that the regurgitated fluid is directed toward the opening 340. The end portion of the mask 365 that surrounds the opening 340 is flexible and is designed to bend backwards as the mask is inserted and comes into contact with the posterior wall of the throat. As the mask is a further inserted, the resiliency of end portion 365 causes the end portion 365 to fold back to its correct orientation. This facilitates insertion of the mask into the patient by preventing or minimising the risk of the tip of the mask digging in or damaging the mucosa of the posterior pharyngeal wall.

Figure 15:
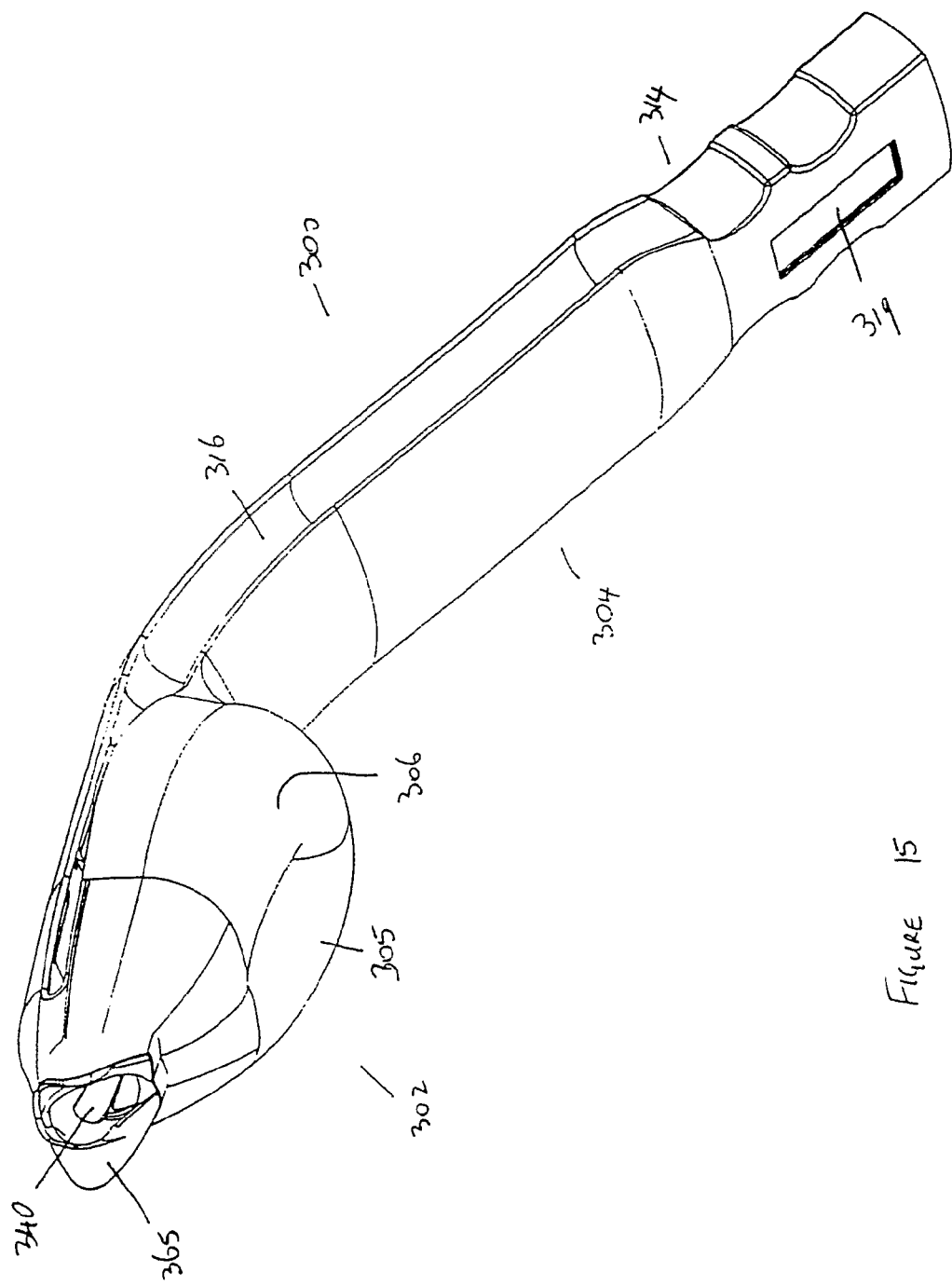
FIG. 15 shows a perspective view of a laryngeal mask in accordance with another embodiment of the present invention.
Figure 18:
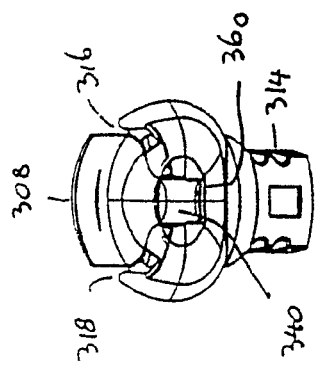
FIG. 18 shows an end view of the laryngeal mask shown in FIG. 15.
Figure 19:
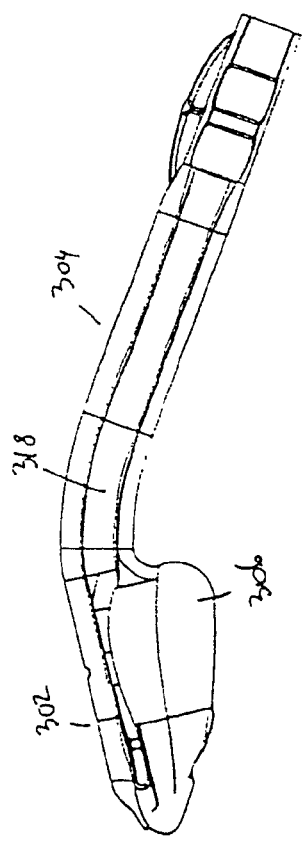
FIG. 19 shows a side view of the laryngeal mask shown in FIG. 15.
Figure 20:
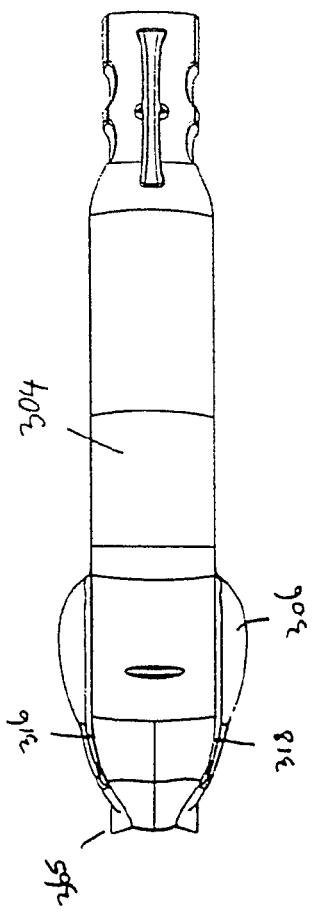
FIG. 20 shows a top view of the laryngeal mask shown in FIG. 15.

Also shown in FIG. 15 is a depression 319 formed at the proximal end of the mask. The depression is provided so that a serial number for the mask can be inserted into the depression. An adhesive or plastic material can then be poured or placed over the serial number to seal the serial number in the mask. This also assist in preserving the serial number during repeated sterilisations in multi-use masks. This depression may be included in all embodiments of the present invention, if desired.

FIGS. 21 to 24 show various views of another embodiment of the present invention. The embodiments shown in FIGS. 21 to 24 is generally similar to the embodiments shown in FIGS. 9 to 14 and, for convenience and brevity of description, the similar features in FIGS. 21 to 24 are not described further. Where the embodiment shown in FIGS. 21 to 24 differs from the embodiment shown in FIGS. 9 to 14 is that the soft flexible membrane is provided with a plurality of reinforcing ribs or legs 380 (shown in phantom outline in FIGS. 21, 23 and 24). In this embodiment, the soft flexible membrane 382 extends between the reinforcing ribs or legs 380. When ventilation gases are provided to the mask via the airway tube 303', the soft flexible membrane 382 expands to come into better contact with the structures surrounding the larynx to thereby improve the seal around the larynx. The reinforcing ribs or legs 380 maintain the shape of the peripheral region of the mask portion 302' to thereby assist in insertion of the mask.

Figure 21:
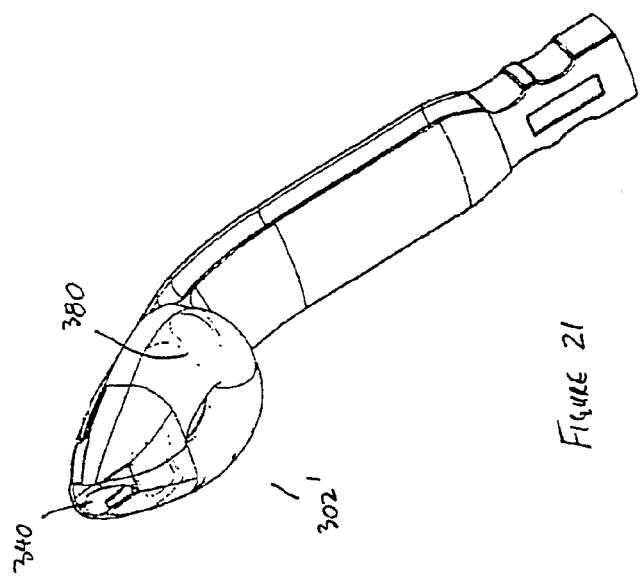
FIG. 21 shows a perspective view of a laryngeal mask in accordance with another embodiment of the present invention.
Figure 22:
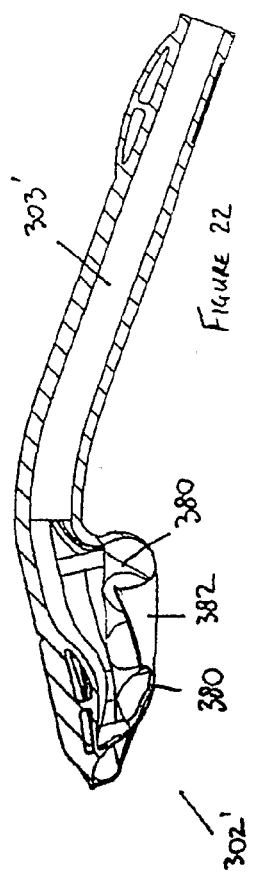
FIG. 22 shows a cross-sectional side view of the mask shown in FIG. 16.
Figure 23:
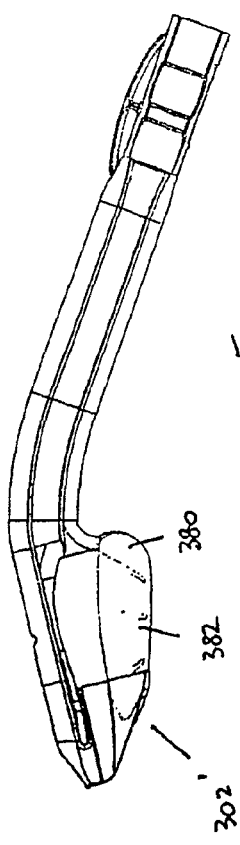
FIG. 23 shows a top view of the laryngeal mask shown in FIG. 21.
Figure 24:
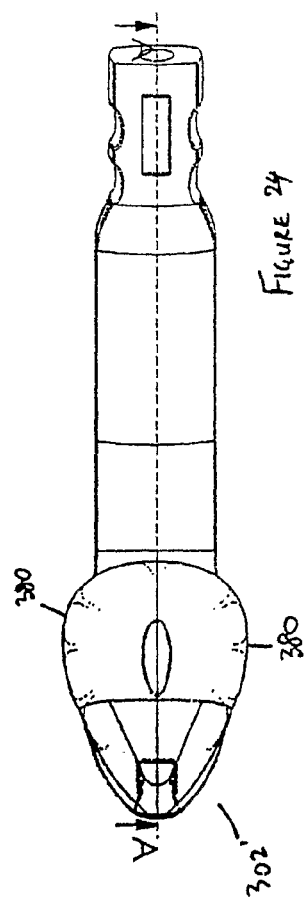
FIG. 24 shows a front view of the mask shown in FIG. 21.
Figure 25:
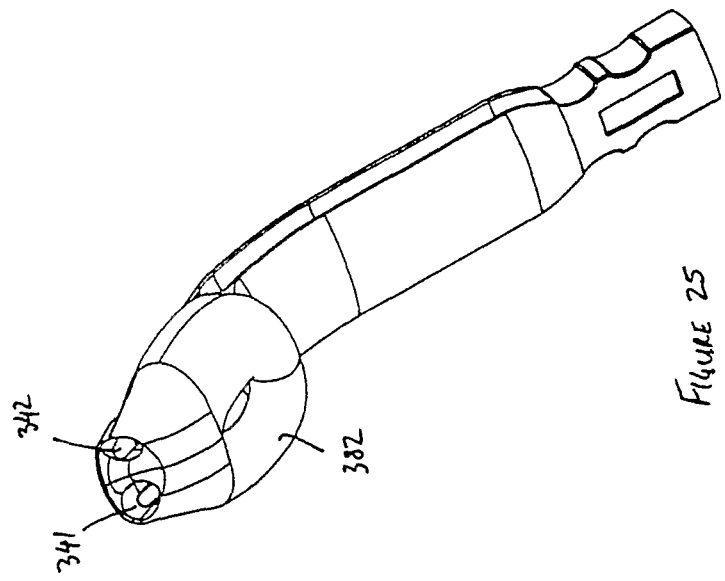
FIG. 25 shows a perspective view of a laryngeal mask in accordance with another embodiment of the present invention.
Figure 26:
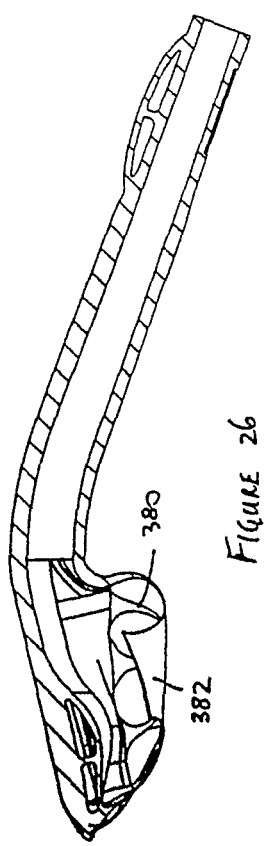
FIG. 26 shows a cross-sectional side view of the mask shown in FIG. 25.
Figure 27:
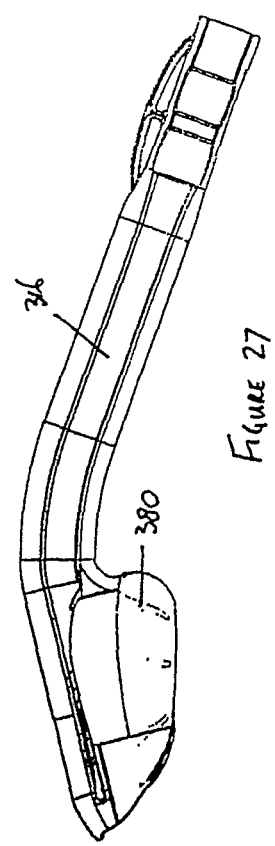
FIG. 27 shows a top view of the laryngeal mask shown in FIG. 25.
Figure 28:
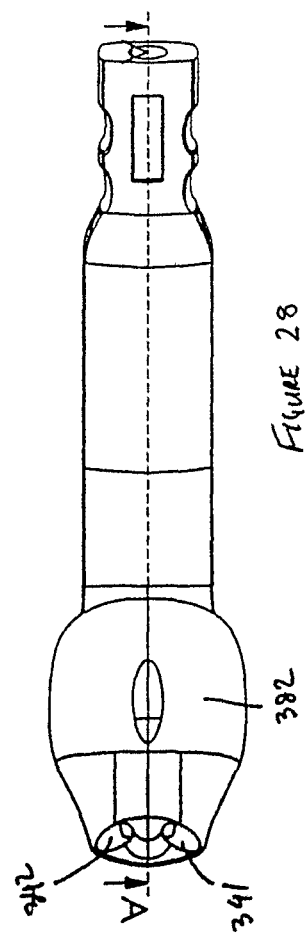
FIG. 28 shows a front view of the mask shown in FIG. 25.
Figure 29:
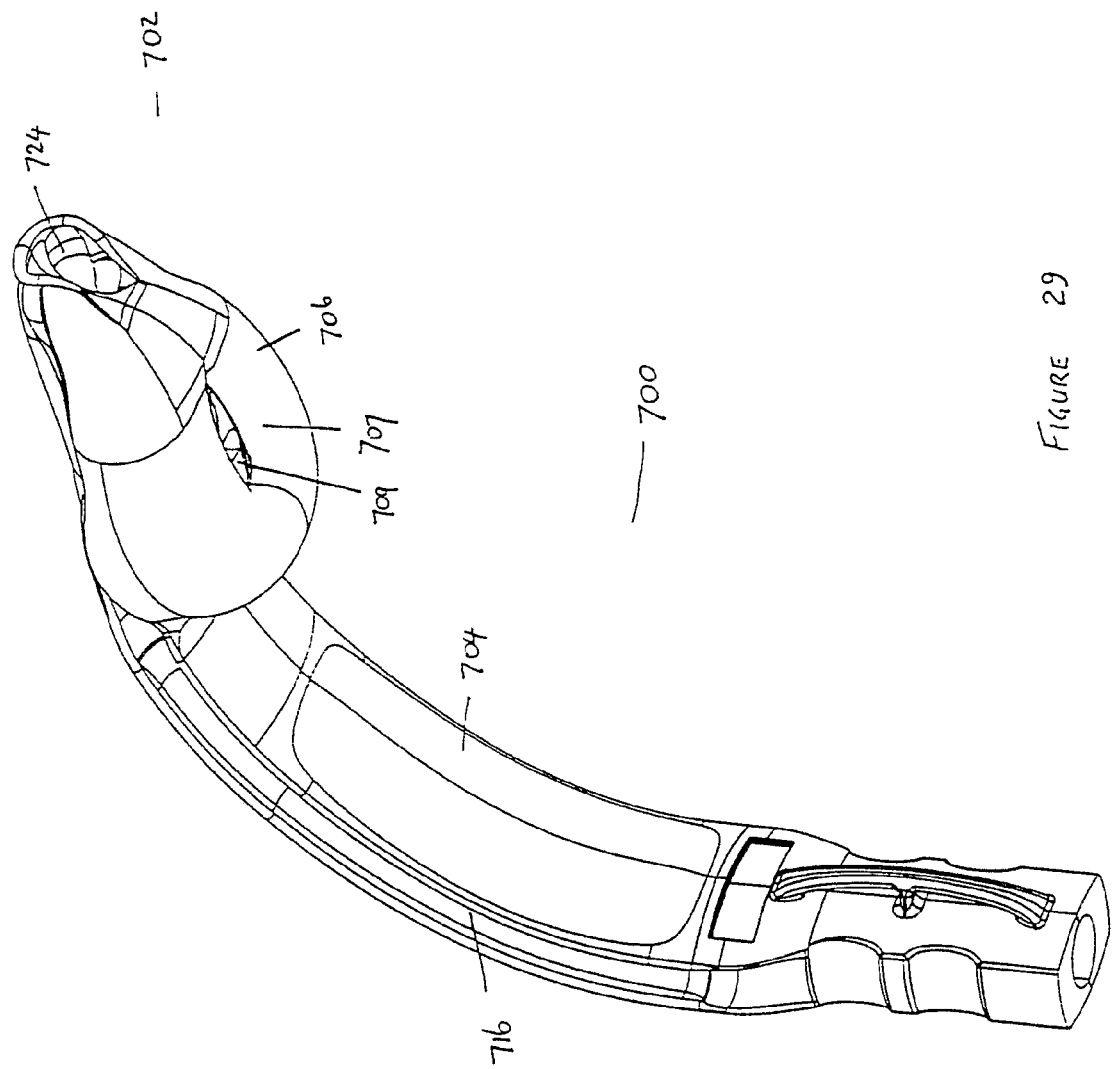
FIG. 29 shows a perspective view, from underneath, of a laryngeal mask in accordance with a further embodiment of the present invention.

FIGS. 25 to 28 show various views of a further embodiment of the present invention. The embodiments shown in FIGS. 25 to 28 is generally similar to the embodiments shown in FIGS. 21 to 24. The main difference is that the opening 340' shown in FIG. 21 is replaced by two openings 341, 342 in the embodiments shown in FIGS. 25 to 28.

FIGS. 29 to 34 show various views of a further embodiment of the present invention. The device 700 shown in FIGS. 29 to 34 has a mask portion 702 and an airway tube 704. As the best shown in FIGS. 30 and 31, airway tube 704 has a curved region 705 located proximally from the mask portion 702. The curved region 705 assists in insertion of the mask into a patient.

Figure 34:
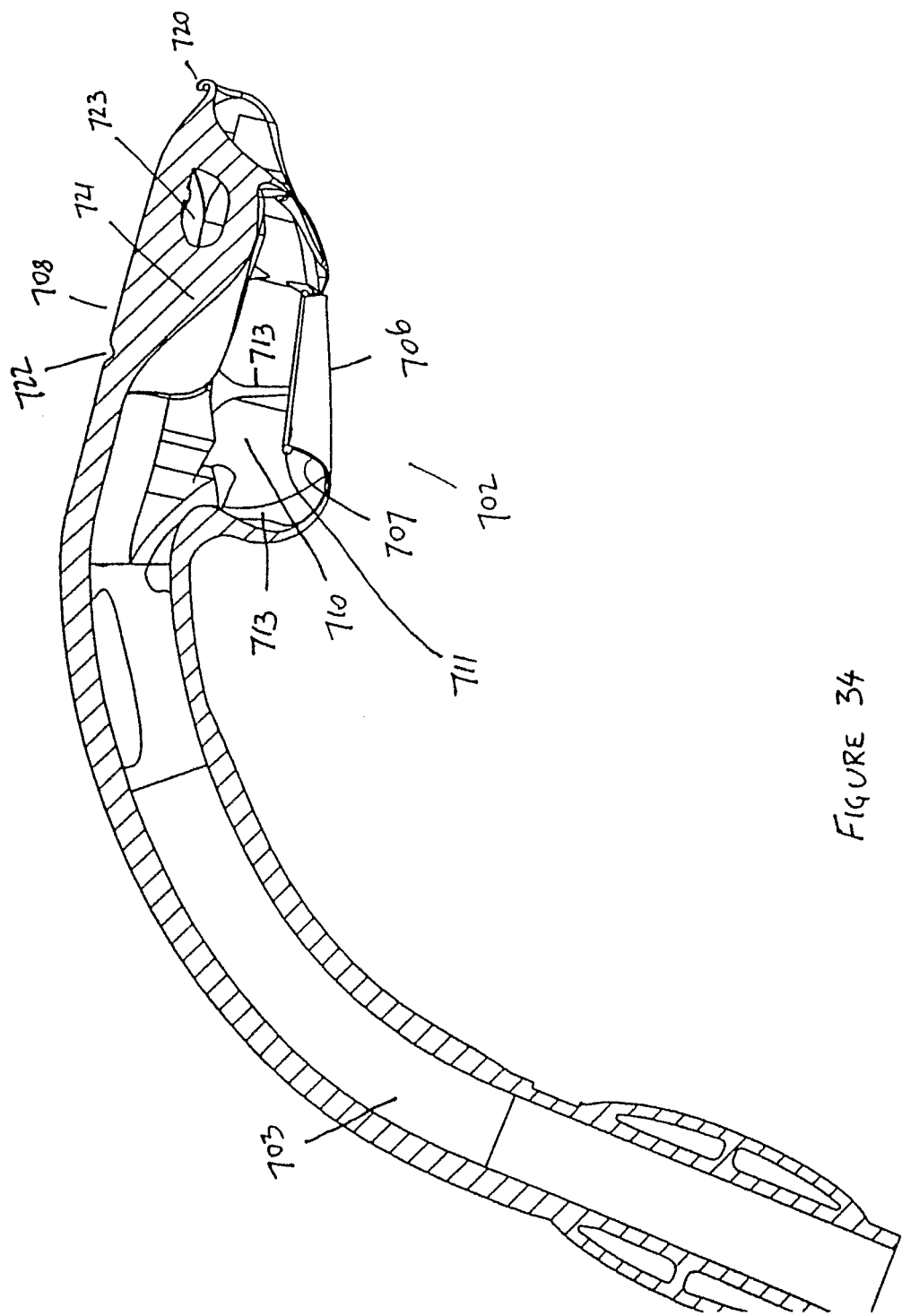
FIG. 34 shows a cross sectional side view of the laryngeal mask shown in FIG. 29.
Figure 35:
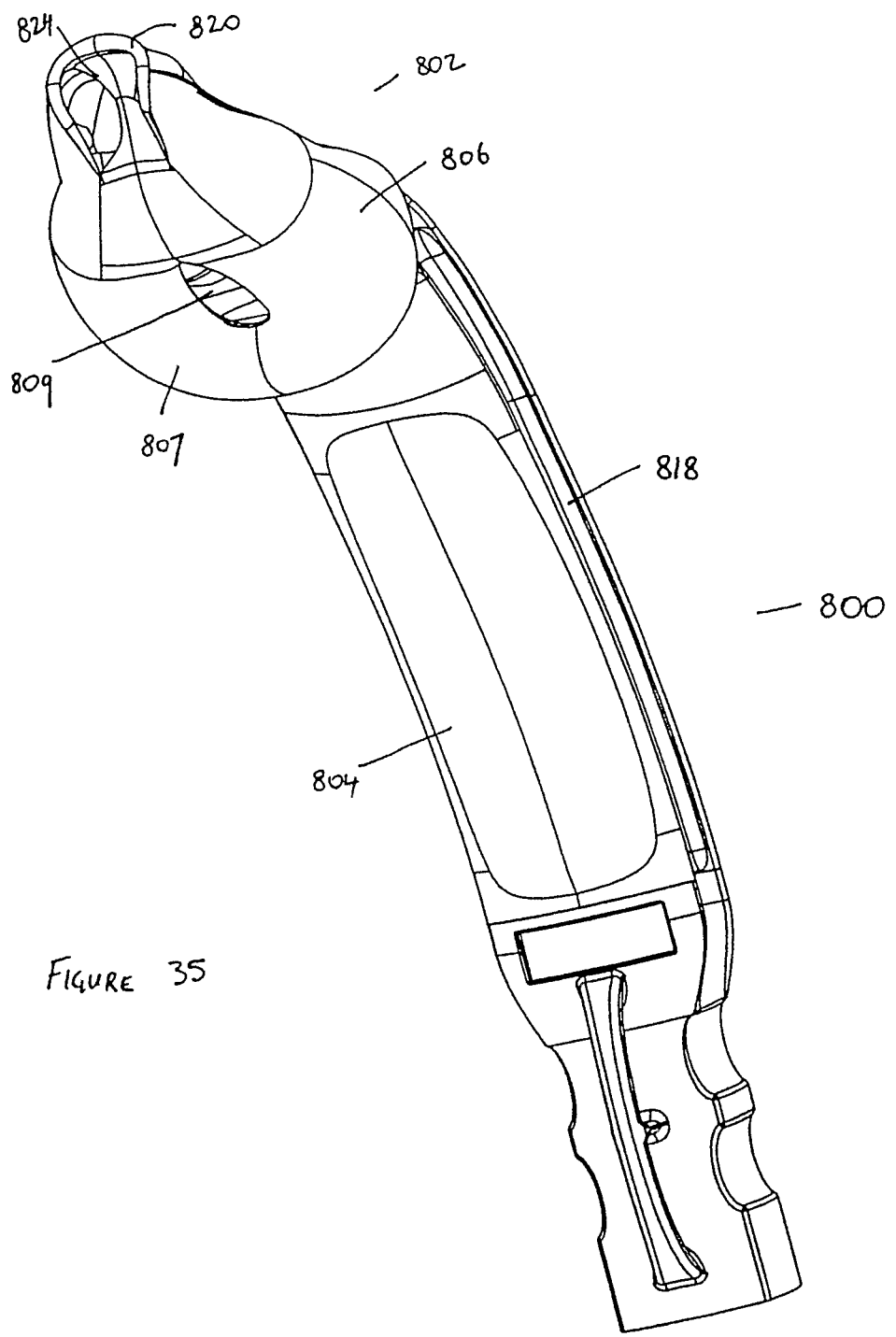
FIG. 35 shows a perspective view of a laryngeal mask in accordance with another embodiment of the present invention.
Figure 36:
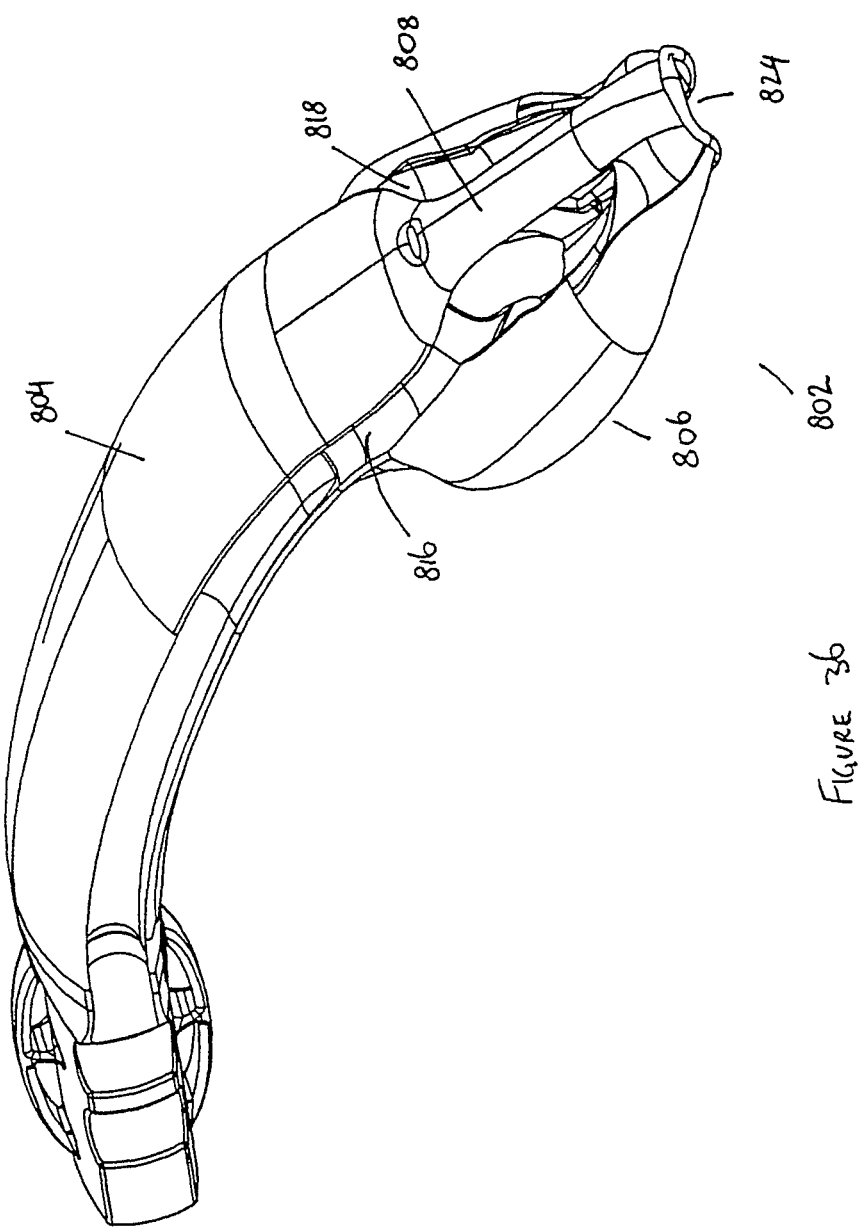
FIG. 36 shows a top perspective view of the laryngeal mask shown in FIG. 35.

The mask portion 702 includes a periphery 706 that defines an upper portion or a dorsal portion of the mask portion 702 that, in use, extends around and forms a seal with the tissues surrounding the larynx of the patient. The mask portion 702 also includes a roof 708 that defines an upper portion or a dorsal portion of the mask 702. As best shown in FIG. 34, a chamber 710 is defined in the mask 702. The chamber 710 is in fluid communication with the airflow tube 703 in airway tube 704. This can also be clearly shown in FIG. 34.

Figure 1:
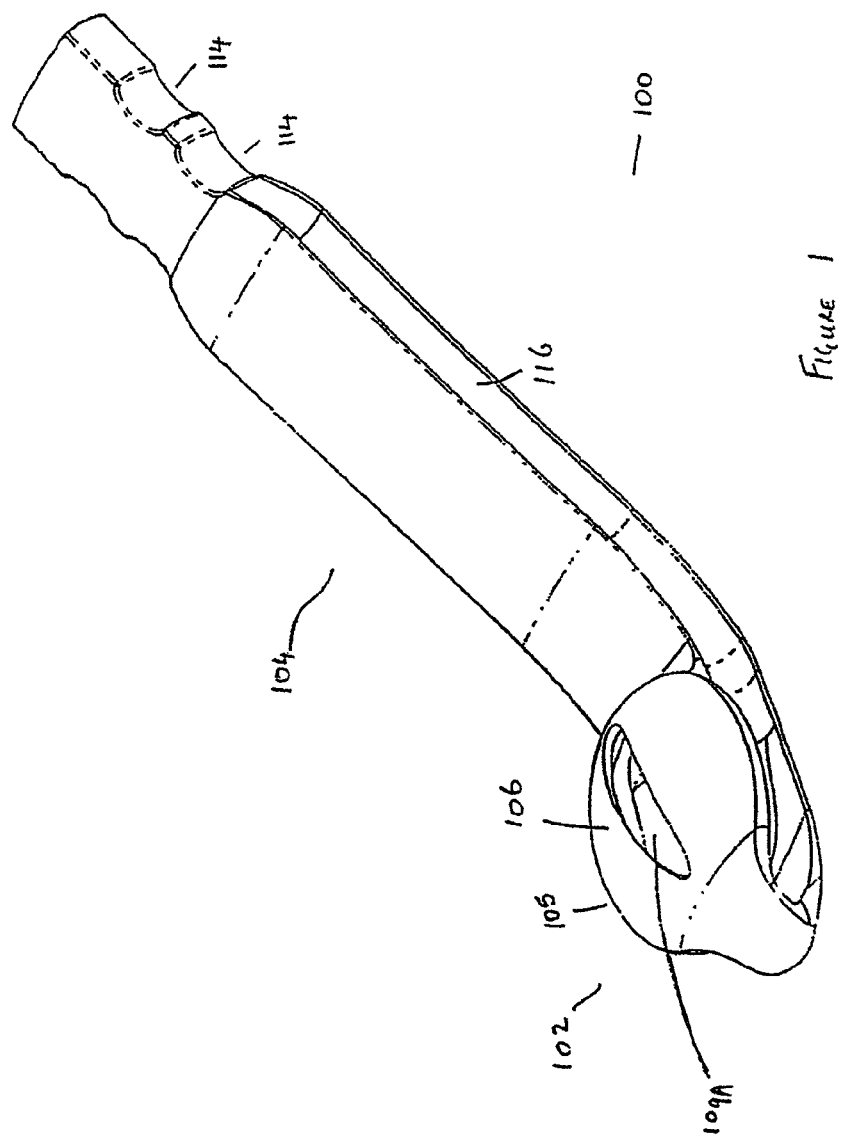
FIG. 1 shows a perspective view of a laryngeal mask in accordance with an embodiment of the present invention.
Figure 30:
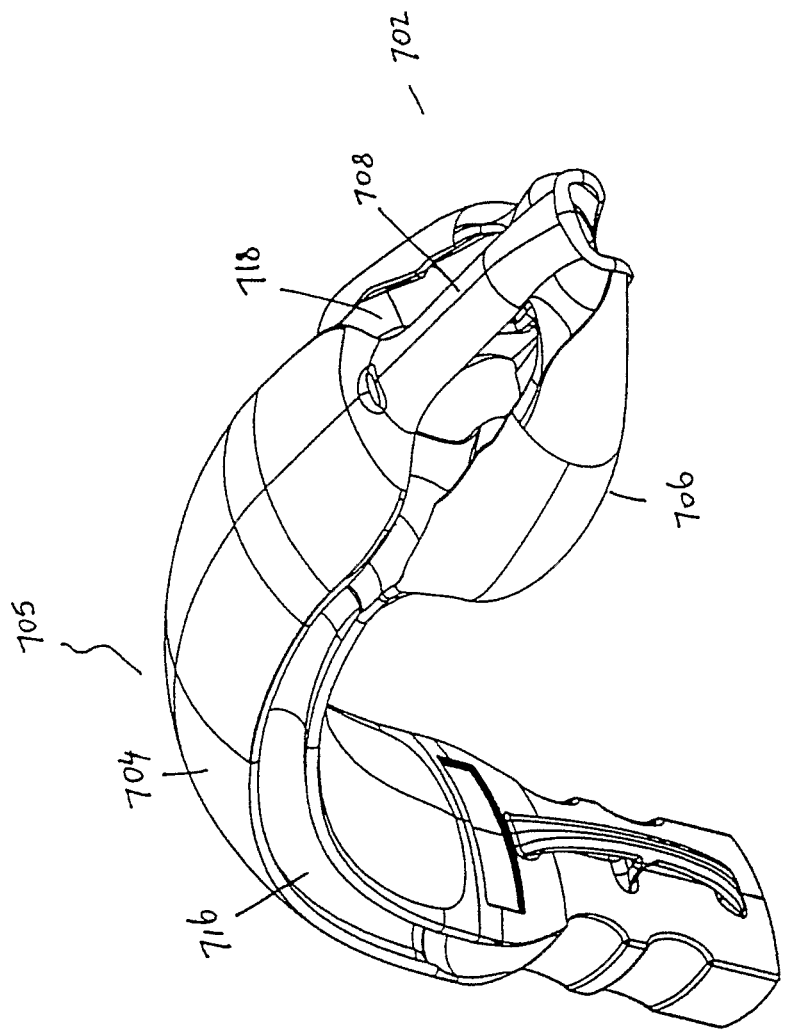
FIG. 30 shows a perspective view, from above, of the laryngeal mask shown in FIG. 29.
Figure 31:
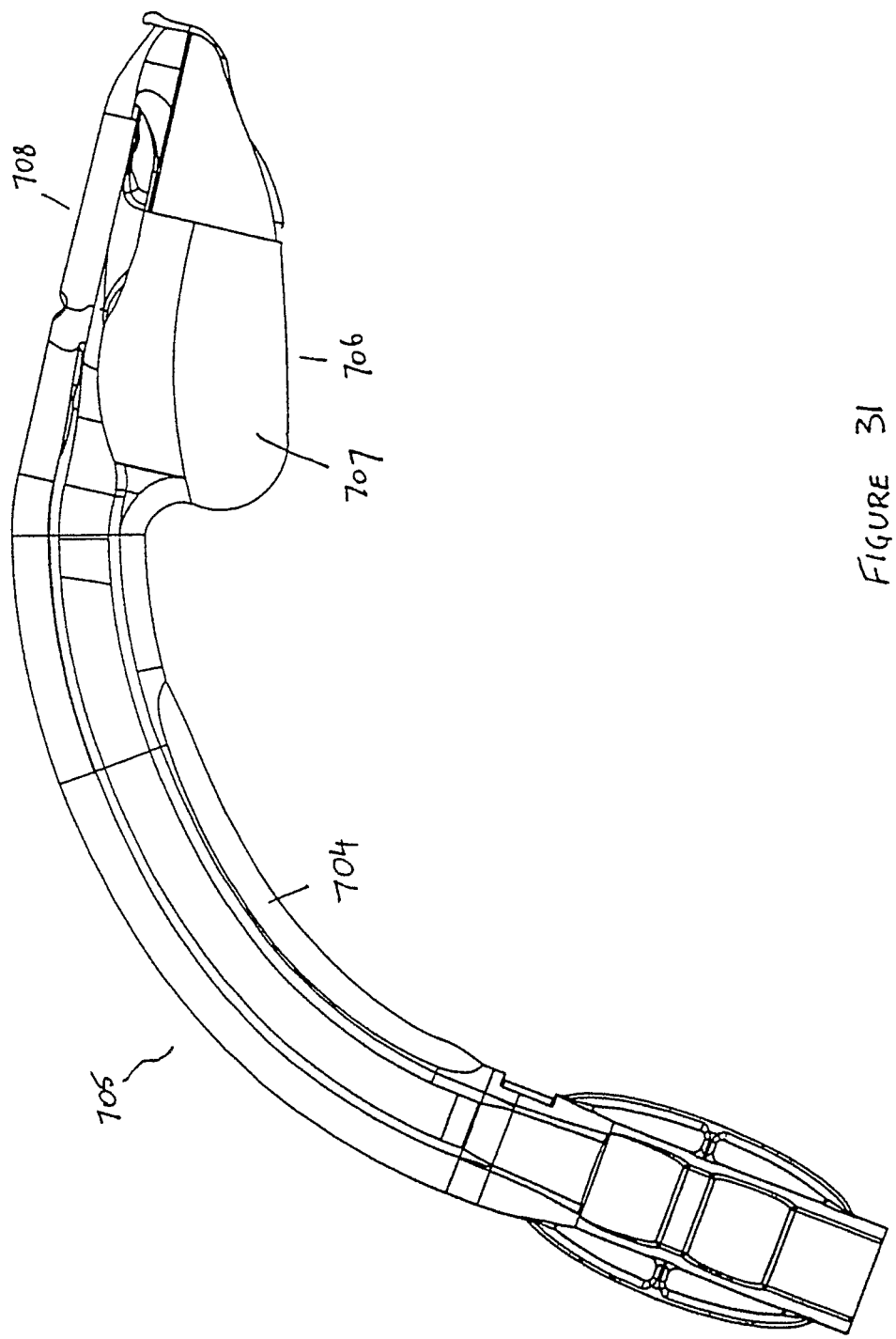
FIG. 31 shows a side view of the laryngeal mask shown in FIG. 29.
Figure 33:
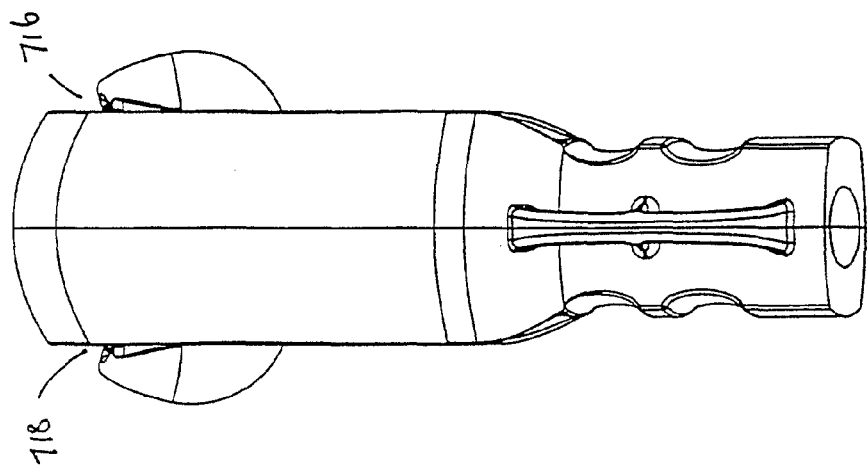
FIG. 33 shows a rear view of the laryngeal mask shown in FIG. 29.
Figure 32:
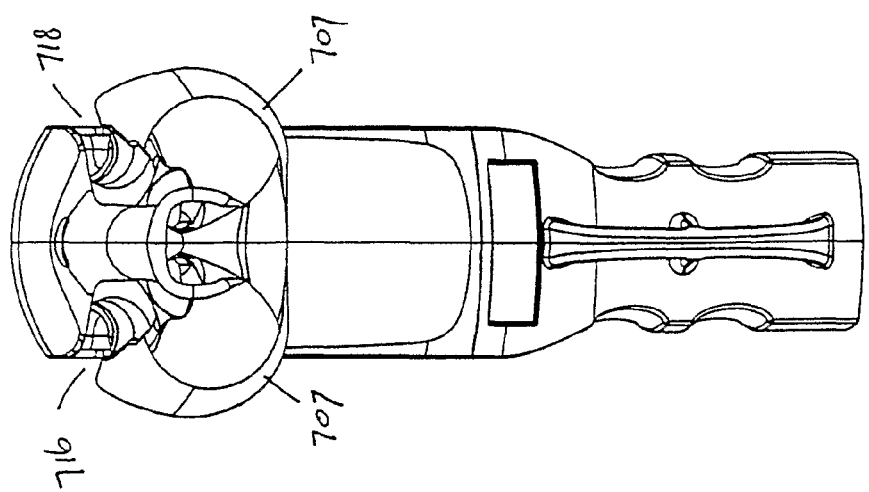
FIG. 32 shows a front view of the laryngeal mask shown in FIG. 29.

The laryngeal mask 700 also includes passageways 716, 718 that extend from the distal portion of the mask towards the proximal portion of the mask. These passageways are similar to passageways 116, 118 as shown in FIG. 1. Passageways 716, 718 can be quite open at their sides in the mask portion 702, as best shown in FIG. 30 and FIG. 32. In this regard, upper portion 708 of the mask portion 702 may be relatively thin in the vicinity of the distal end of the mask portion 702.

The mask portion 702 includes a soft, flexible membrane 707. This soft, flexible membrane 707 defines an opening 709. Opening 709 is in fluid communication with chamber 710 which, in turn, is in fluid communication with airflow tube 703. In this fashion, ventilation gases or other gases supplied via the airway tube 704 passed through the larynx and into the trachea of the patient.

As the shown in FIG. 34, a ring of thicker material 711 extends around the periphery of the opening 709. This strengthens the opening 709 and assists in maintaining the shape of the opening of the mask. FIG. 34 also shows that the perpihery 706 includes reinforcing ribs 713 that strengthen the peripheral region and assist in maintaining the shape of the peripheral region. The reinforcing ribs 713 may be simply produced by forming thickened regions of the desired shape in the peripheral portion 706 of the mask.

The distal end of the mask portion 702 includes an upwardly turned lip 720 to facilitate insertion into the patient. A notch or groove 722 is also formed on the upper surface all dorsal surface of the mask portion 702. The distal tip also includes an opening 724 which is in fluid communication with passengways 716, 718. Opening 724 is generally similar to the opening 340 shown in FIG. 15.

A wall 721 is positioned between passageways 716 and 718 in the mask portion 702. This wall stiffens the mask portion so that the mask is relatively stiff at its upper or dorsal portion. This assists in maintaining the shape of the mask. An opening 723 is formed in wall 721 towards the distal end of the mask and this opening allows for fluid communication between passage 716 and passage 718.

Other features of the embodiments shown in FIGS. 29 to 34 are generally similar to the features of the mask as shown in FIGS. 15 to 29 and need not be described further.

FIGS. 35 to 39 show various use of a laryngeal mask in accordance with another embodiment of the present invention. The mask shown in FIGS. 35 to 39 has a number of features in common with the mask shown in FIGS. 29 to 34 and, for convenience, similar features will be denoted by the similar reference numerals, but with the use of an "8" rather than a "7" as the first number of the reference numerals. These features need not be described further.

Where the mask 800 differs from the mask 700 is that the curvature 805 in the airway tube 803 is significantly less than the curvature in airway tube 703 of mask 700.

FIGS. 38A to 38D show various end sectional views of the mask portion 802 of the laryngeal mask 800. These views clearly shown the thin membrane 107, the thickened ring 813 that surrounds the opening 809 and also the particular shape of the membrane 807 that acts to catch ventilating gases that are provided to the patient so that the membrane is urged towards the tissues surrounding the larynx to thereby improve the effectiveness of the seal around the larynx. FIGS. 38A to 38D also show the relatively strong or relatively stiff central spine 850 of the mask and thickened circumferential regions 852 of the peripheral portion of the mask portion. These make the mask stiffer and the thickened circumferential regions make the periphery firmer to open up the airway cavity and provide additional support to the ribs 813.

Figure 39:
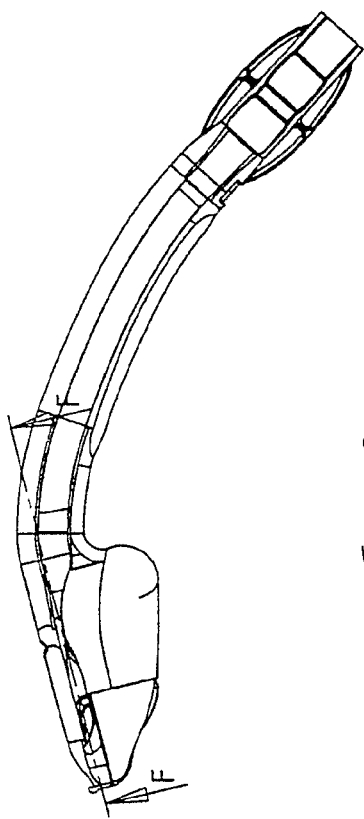
FIG. 39 shows a perspective view of a laryngeal mask in accordance with another embodiment of the present invention.
Figure 39:
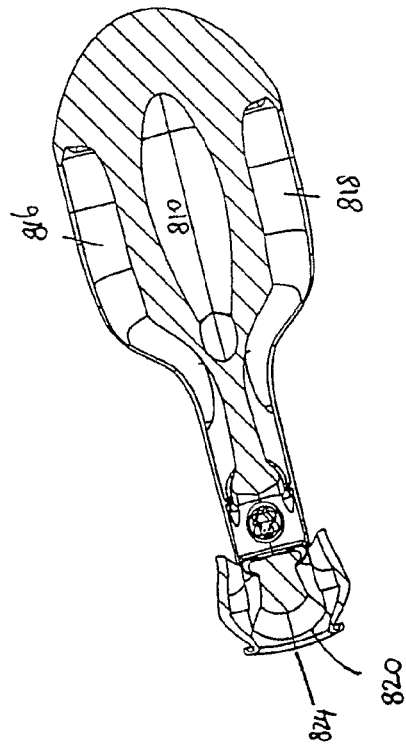

FIG. 39B shows a cross sectional plan view taken along line F-F shown in FIG. 39. This view clearly shows the chamber 810 and the dorsally extending inner wall 890 of the soft flexible region 806. The dorsal end 892 of the inner wall 890 defines the opening of the airway chamber through which ventilation gases or anaesthetic gases exit the mask portion.

It can also be seen that the mask portion of the device shown in FIGS. 29 to 39 has a narrower distal portion than the device as shown in FIGS. 1 to 28 (when viewed from above). This assists in ensuring that the distal end will enter the upper oesophagus (that is, the oesophageal sphincter) without compromising the cavities and the effective flow of fluid from the oesophagus to the passages 816, 818.

A description of the use of the airway device in accordance with embodiments of the present invention described in FIGS. 1 to 39 will now be provided.

Mostly during anaesthesia and always at the time of resuscitation, patients are placed on their back. There may be vomitus, secretions or other materials such as water and blood present in the pharynx. These materials normally gravitate to the posterior pharyngeal wall, being the lowest area.

When the airway device in accordance with the most preferred embodiments of the present invention (such as that shown in FIGS. 9-39 is introduced into the patient, the longitudinal oval opening (e.g. opening 208) will glide over the patient's tongue and be sealed by the tongue. When the distal end of the mask hits the posterior pharyngeal wall, the end part of the mask will bend ventrally, facilitated by the presence of the dorsal notch or groove. This will enable the mask to pass downwards to the larynx. Pushed further, the distal end of the mask will slide under the larynx, which again will then glide over the ramp part to reach the top of the cricoid cushion. The membrane part of the mask at that point, with the cricoid cushion, being pressed posteriorly by the cricoid cartilage, produces a comfortable seal at the front distal part of the mask. This is where the spring action of the cricoid cushion and the sling action of the distal end of the membrane part help to form the seal. Also at this point, when pushed further, the larynx snugly gets into the airway cavity with the sides of the larynx cover to be sealed by the sides of the soft membrane part of the face (or ventral portion) of the mask.

The larynx gets to rest inside the airway cavity (or chamber) of the mask. The proximal part of the mask will form a comfortable seal with the posterior part of the tongue to complete the seal around the larynx with the membrane face part of the mask.

During the downward travel of the mask, it moves with its ventral part facing upwards (when the patient is lying on his or her back) with the opening of the mask in contact with the tongue and avoids any material from entering the airway cavity. Then, the end part of the mask gets under the larynx to make it glide over the ramp to enable entry of the larynx into the airway cavity (internal chamber of the mask). Now the mask comes to a rest, the taller proximal and vertical part of the mask fits behind the tongue and the larynx on the other side of the wall within the airway cavity facing the airway tube.

The walls of the mask, including the membrane part, exert as a circumferential seal against the periphery of the larynx by virtue of their structures and shape.

While the mask is positioned properly, the internal cricoid pressure cushion retains its cavity by virtue of its structure and helps to maintain the fluid communication with the other end of the oesophagus and the sump cavities or passageways of the mask, and enable regurgitated materials to be evacuated.

When intermittent positive pressure ventilation is applied, the increasing pressure inside the airway cavity will circumferentially expand the mask due to its resilient nature. But due to the fact that the mask is made of varying thicknesses, its expansion varies considerably in different parts of the mask. This expansion tends to increase the seal around the mask in all directions against the pharyngeal walls.

As the part of the mask facing the anterior pharyngeal wall around the laryngeal opening is also made of differential thicknesses, the thinner parts expand the most and exert further pressure against the tissues that they are in contact with.

Increases in pressure during IPPV will proportionately increase the seal around the larynx, thus help prevent any leakage during IPPV. Further, as the increased pressure is only applied during the high-pressure part of the IPPV cycle, the increased pressure against the tissues is intermittent, thereby minimising the disruption of blood flow to the tissues caused by that increased pressure and thereby minimising trauma to those tissues and discomfort to the patient.

Of particular note of the laryngeal mask shown in one or more of the embodiments in FIGS. 1 to 39 are the following features:

- the mask has a blunt/wide distal end;
- the mask has an upturned or dorsally turned tip;
- the mask has a ramp for the larynx to slide over during insertion;
- the mask may have one or two large openings at the distal end opening into the upper oesophagus;
- the opening(s) may lead to a sump cavity or fluid drainage passageways;
- there is a facility for drainage from the mouth cavity to a sump area;
- there is direct drainage behind the tongue into a suction tube;
- the sump cavity may be connected to the mouth by way of grooves or tubes;
- the dorsal surface of the mask may be straight or curved longitudinally and it may be straight or curved from side to side. The dorsal surface may be provided with a groove at a mid part or a distal end thereof;
- the sump cavity may form an elevation or a prominence extending ventrally to come into contact with the cricoid cartilage and therefore push the cricoid and larynx ventrally to keep the upper end of the oesophagus open to facilitate easy drainage of oesophageal fluid to the exterior ("internal or posterior cricoid pressure");
- the mask has a large airway cavity, which allows a better breathing space;
- spring action of the walls keeps the breathing cavity patent and isolated from the drainage area;
- the ventral membrane from the walls of the airway cavity will stop or control leakage or overflow during intermittent positive pressure ventilation (IPPV);
- reinforcing ribs or legs keep the cavity in shape and, in combination with the walls, keep the anterior pharyngeal wall away from the post laryngeal wall, thereby forming the airway cavity;
- the membrane portions between the reinforcing ribs or legs will bulge out and push and keep up the wall during IPPV and stop or control the leakage of IPPV pressure;
- the membrane can come into sound contact with the piriform recess, thereby minimising the likelihood that the piriform recess will provide a site for leakage;
- when inserted, the larynx will glide over the ramp and enter the laryngeal opening of the mask and lodge inside the airway cavity chamber;
- the provision of drainage passages on the mask produces two longitudinal elevations on the posterior surface of the airway cavity, forming a longitudinal gutter in the middle which leads to the opening of the patient's airway tube. These two elevations stop the laryngeal opening from being blocked by being opposed to a flat surface. Therefore, the two elevations with the gutter in the middle facilitates better breathing; and
- previous laryngeal masks having inflatable cuffs have, in some instances, caused nerve damage due to their constant pressure on the nerves, especially the recurrent laryngeal nerve, hypoglossal nerve and lingual nerve. The mask in accordance with the embodiments shown in FIGS. 1 to 39 is much softer and does not exert continuous positive pressure, but rather only exerts high pressure during the maximum pressure exerted during IPPV. This maximum pressure is only exerted for a short duration. The present mask is shorter, softer and maximises the IPPV. The maximum pressure exerted by the mask is only applied for a fraction of the inspiratory phase of the respiratory cycle and, moreover, the maximum pressure applied by the mask is only at the maximum inflatory pressure of the lung ventilation. Therefore, this lessens the possibility of nerve damage, as a result of the pressure applied by the mask to the patient's tissues being related to the ventilation pressure, not to the pressure applied to an inflatable cuff.

In preferred embodiments, the membrane portion includes a portion that extends from around the opening of the airway chamber and, in use, lies generally parallel to the underlying laryngeal structures. This membrane portion extends outwardly from the opening in the airway chamber and then extends upwardly towards the dorsal side of the mask. This shape enhances the ability of the mask to expand with the ventilation pressure supplied via the airway tube and therefore enhances the ability of the mask to form a seal.

The mask of preferred embodiments of the present invention is a new supraglottic airway device designed to be user-friendly and to overcome most of the difficulties associated with other available supraglottic airway devices. The device may be made from a single injection moulding.

Unlike other supraglottic airway devices where a large size is needed to achieve a good seal, with the device of the present invention only a relatively small size is necessary. This, in combination with its design, make it easy to insert. The device also locates itself easily into position when it is introduced. As there is no need to inflate a cuff (in preferred embodiments) or to spend time repositioning the mask, insertion is quick and simple.

The device can be introduced with continuous high-volume, high pressure suction attached to the suction tube incorporated into the device. The longitudinal airway opening of the mask glides over the patient's tongue and is sealed by the tongue all along until it positions itself on the larynx. When the distal end of the mask hits the posterior pharyngeal wall, the end part of the mask bends ventrally, facilitated by the presence of the dorsal notch or groove. This enables the mask to pass downwards towards the larynx. Pushed further, the distal end of the mask slides under the larynx, which glides over the ramp part of the mask to reach the top of the cricoid cushion. The membranous part of the mask with the cricoid cushion forms a comfortable seal at the front distal part of the mask. This is where the spring action of the cricoid cushion and the sling action of the distal end of the membranous part help to form a seal. As the mask is pushed in further, the laryngeal inlet enters the airway cavity with the membranous part applying a seal around the larynx. The laryngeal inlet rests inside the airway cavity, achieving a clear airway. The proximal firmer part of the mask elevates the root of the tongue, enhancing the patency of the airway further and also complementing the seal formed by the membranous part.

When the mask is initially being inserted (with the patient supine), as it passes behind the tongue the airway opening of the mask remains in close contact with the dorsal surface of the tongue, and is protected by the tongue from any foreign materials (such as fluid and blood) from entering the airway cavity, since these gravitate to the back of the pharynx.

Whilst the device is being inserted, the distal opening of the mask with its sump cavity is always at the forefront, actively sucking and clearing all the unwanted materials along the way. This continues in situ during its use as well as whilst the mask is being removed. Thus, the area around the mask will be clear of any unwanted materials at all times, leaving little chance for aspiration. This scavanging action is also enhanced by the presence of the two longitudinal openings on either side of the mask leading into the sump area.

While the mask is in position, the internal cricoid pressure cushion will retain the patency of its cavity, which is a part of the sump cavity, by virtue of its structure, thus enabling fluid communication with the upper end of the oesophagus at all times.

Two tubes may be built into the stem of the device along the airway tube (one on either side) and the tubes are in fluid communication with the sump cavity at their distal end. One of the tubes evacuates any material from the sump cavity. The other tube vents air into the sump cavity while the suction is an operation to prevent a build-up of any negative pressure in the sump cavity and to ensure its action as a sump.

The airway tube of the device may have an inbuilt bite block that runs along its entire length. Although this bite block is sufficiently rigid to ensure patency of the airway in the event that the patient bites the tube, it is soft enough to not cause damage to the patient's teeth.

It is possible that the patient may bite the airway during removal with the mask still inside the mouth and the airway opening facing the surface of the tongue. In that situation, an airway obstruction may occur. However, the two tubes in the stem alongside the airway tube will then function as additional airways to allow air entry and maintain oxygenation.

Securing the device in position in the patient during transfer, transport and ventilation is added by a series of depressions and loops built into the proximal end of the airway tube.

In a further embodiments of the present invention, a further similarly shaped diaphragm or membrane portion may be provided as an extension of the central region of the mask portion. This further diaphragm or membrane portion may result in the laryngeal mask having a "double membrane arrangement" if the laryngeal mask is provided with a second diaphragm or membrane portion. Alternatively, the further diaphragm or membrane portion may be provided on the ventral side of an inflatable cuff mask.

Figure 40:
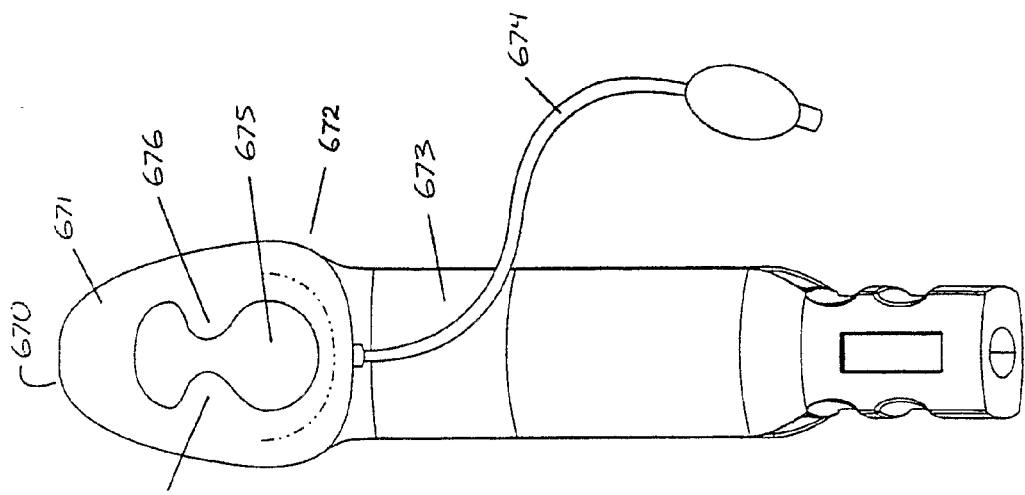
FIG. 40 shows an underneath view of another embodiment of a laryngeal mask in accordance with the present invention.

FIG. 40 shows a further embodiment in accordance with the present invention. In particular, FIG. 40 shows a laryngeal mask 670 having an inflatable cuff 672 formed in the mask portion 671 thereof. An airway tube 673 is formed with or joined to the mask portion 671. An inflation tube 674 is used to inflate the inflatable cuff 672.

The mask portion 671 defines a chamber 675. A peripherally extending region 676 is formed in the chamber 675 and region 676 acts as the cricoid contacting portion.

Figure 41:
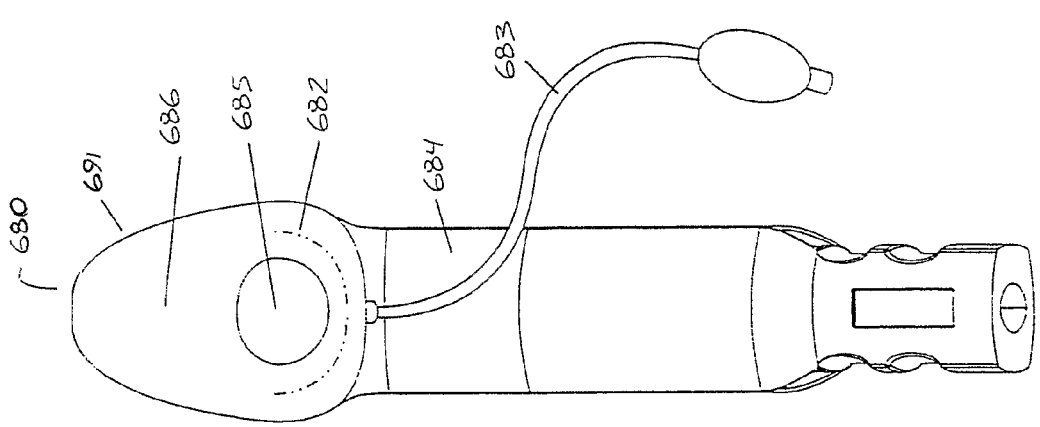
FIG. 41 shows an underneath view of a further embodiment of a laryngeal mask in accordance with the present invention.

FIG. 41 shows a laryngeal mask 680 having a mask portion 681 that has an inflatable cuff 682. The inflatable cuff is inflated via inflation tube 683. The laryngeal mask 680 also includes an airway tube 684. The chamber 685 is defined in the mask portion 681, with the chamber 685 being in fluid communication with the airway tube 684. A cricoid contacting the region 686 is formed in the distal portion of the mask portion 681.

Figure 42:
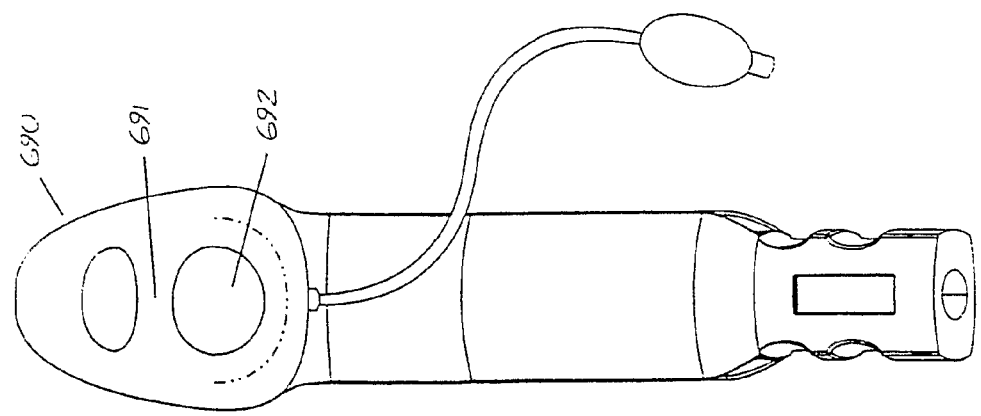
FIG. 42 shows an underneath view of yet another embodiment of a laryngeal mask in accordance with the present invention.

FIG. 42 shows another embodiment of a mask in accordance the present invention. The mask 690 shown in FIG. 42 is generally similar to the mask 670 shown in FIG. 30 and the common features need not be described further. The mask 690 shown in FIG. 42 includes an elevated region 691 that extends across the chamber 692. The elevated region 691 forms the cricoid contacting region of the mask.

The laryngeal mask shown in FIGS. 43 to 47 is especially suitable for use in intubating patients. The mask 900 has a number of features in common with the mask is shown in FIGS. 1 to 39. For brevity of description, these common features will largely not be described further.

The mask 900 includes a cricoid cushion 902 (which equates to the cricoid contacting portion of earlier embodiments). As can be seen from FIGS. 43 and 44, the cricoid cushion 902 includes a ventrally extending portion. This ventrally extending portion forms part of the inner dorsal wall of the mask. The mask also includes a flexible membrane 904 having a thickened ring of material 906 extending around an opening in the middle portion of the membrane.

Located just proximal of the cricoid cushion 902 is a further ventrally extending region 908. This region terminates at its distal end at 910. The inner dorsal wall then extends dorsally to form a notch or recess at 912. The dorsal-most extent of this notch or recess 912 defines the beginning of the cricoid cushion 902.

The flexible membrane 904 carries a dorsally extending barrier or flap 914. The barrier or flap 914 extends dorsally from the opening in the barrier or flap. The barrier or flap 914 has a base that is broader than its tip. In other words, as the barrier or flap 914 extends in a dorsal direction, its width decreases.

FIGS. 45 and 46 show the barrier or flap 914 being positioned such that it lies adjacent the cricoid cushion 902 (or, in other words, so that the barrier or flap 914 is adjacent the inner dorsal wall). The barrier or flap 914 moves to this position when the mask 900 is properly inserted into a patient. Insertion of the mask causes deformation of the membrane 904, which effectively displaces the barrier or flap 914 to the position as shown in FIGS. 45 and 46. As can be seen, the free end of the barrier or flap 914 is positioned dorsally upwardly from the distal end of the ventrally extending region 908. Therefore, the ventral extension 910 "protects" the end of the barrier or flap 914 from coming into contact with an end of an endotracheal tube, fibre-optic light guide, or similar equipment being passed through the mask.

When an endotracheal tube 920 is inserted through the mask, the end of the endotracheal tube contacts the ventral extension 910 and is guided downwardly. Continued insertion of the endotracheal tube causes the end to slide past the barrier or flap 914 and thereafter exit the opening in the mask. As the mask is properly positioned over the larynx, the endotracheal tube will enter the trachea of the patient when it extends through the opening in the mask. This is shown in FIG. 47 were endotracheal tube 920 is extending through the opening in the mask.

The laryngeal mask shown in FIGS. 43 to 47 can be readily positioned in a patient and allows for quick and effective integration of the patient. By virtue of the tapering width of the barrier or flap 914, translating gases provided by the airway tube can access all regions of the flexible membrane 904 to thereby ensure that a good seal between the mask and the structures around the larynx is obtained. This embodiment can be put into routine use in a similar manner as described with reference to previous embodiments. However, the embodiment of FIGS. 43 to 47 can also be used in emergency situations where it may be necessary to intubate a patient or in situations where an anesthetist may wish to keep open the option of inserting an endotracheal tube during a procedure without having to change the laryngeal mask.

Those skilled in the art will appreciate that the present invention may be subject to variations and modifications other than those specifically described. It will be understood that the present invention encompasses all such variations and modifications that fall within its spirit and scope.

What is claimed is:

1. A device for maintaining an airway in a patient, the device comprising:
    a mask portion; and
    an airway tube connected to or formed with the mask portion for passing gas to the patient's larynx when the mask portion is properly inserted into the laryngo pharynx;
    the mask portion having an opening through which ventilation gases exit the mask portion, the mask portion further comprising a soft, flexible portion positioned on a ventral side of the mask portion, the soft flexible portion having a part that extends from a structure comprising thicker wall thickness or less flexibility than the soft, flexible portion, the soft, flexible portion including a ventral wall portion positioned such that when the mask portion is inserted into a patient, the ventral wall portion lies generally parallel to the tissues surrounding the laryngeal inlet of the patient, the soft flexible portion further comprising an inner wall that extends in a dorsal direction from the ventral wall portion, the inner wall further comprising a portion of thicker material that extends around the opening, and
    whereby the soft, flexible portion is arranged in the completed device such that application of pressurised gas to the airway tube urges the ventral wall portion of the soft, flexible portion into contact with the tissues surrounding the laryngeal opening or the anterior pharyngeal wall to thereby form a seal with the larynx when the mask portion is positioned in the laryngo pharynx to thereby prevent ingress of extraneous fluids into the larynx and wherein the pressurised gas also pushes the inner wall outwards and urges the inner wall into sealing contact with tissues underlying the inner wall.

2. The device as claimed in claim 1, wherein the soft, flexible portion of the mask portion extends in a ventral direction from a wall section of the mask portion, the soft, flexible portion having a thinner wall thickness than the wall thickness of the wall section.

3. The device as claimed in claim 1, wherein the inner wall defines or includes the opening through which ventilation gases exit the mask portion.

4. The device as claimed in claim 1, wherein a distal end of the opening of the mask portion through which ventilation gases are supplied to the patient is provided with a sloped region or a ramp.

5. The device as claimed in claim 1, wherein the mask portion further includes a cricoid contacting portion that extends towards the cricoid cartilage and abuts with the cricoid cartilage when the mask portion is properly inserted, the cricoid contacting portion being adapted to form a seal in the vicinity of the cricoid cartilage or upper oesophagus.

6. The device as claimed in claim 5, wherein the cricoid contacting portion has a resilient and conformable structure that, in use, abuts with the cricoid cartilage.

7. The device as claimed in claim 5, wherein a dorsal side of the cricoid contacting portion includes one or more transversely extending openings facilitating fluid communication between passageways on either side of the mask portion.

8. The device as claimed in claim 1, wherein the mask portion includes a distal portion that extends past the cricoid cartilage when the mask portion is properly inserted.

9. The device as claimed in claim 1, wherein the device includes a ventral curvature at a proximal portion of the mask portion, or near where the mask portion and airway tube join or merge.

10. The device as claimed in claim 1, wherein the soft flexible portion is shaped such that it extends into and fills the piriform recess when the mask portion is supplied with ventilation gas.

11. The device as claimed in claim 1, wherein the soft, flexible portion has a wall thickness less than that of the rest of the mask portion.

12. A device for maintaining an airway in a patient, the device comprising:
    a mask portion;
    an airway tube connected to or formed with the mask portion for passing gas to the patient's larynx when the mask portion is properly inserted into the laryngo pharynx;
    one or more openings at or near a distal end of the mask portion, the one or more openings being associated with a pair of longitudinally extending passageways or cavities that allow fluid communication between the oesophagus and the throat region when the mask portion is inserted into the patient, and
    one or more transversely extending openings facilitating fluid communication between the pair of passageways;
    the mask portion having an opening through which ventilation gases exit the mask portion, the mask portion further comprising a soft, flexible portion positioned on a ventral side of the mask portion, the soft, flexible portion having a part that extends from a structure comprising thicker wall thickness or less flexibility than the soft, flexible portion, the soft, flexible portion including a ventral wall portion positioned such that when the mask portion is inserted into a patient, the ventral wall portion lies generally parallel to the tissues surrounding the laryngeal inlet of the patient, the soft, flexible portion further comprising an inner wall that extends in a dorsal direction from the ventral wall portion; and whereby the soft, flexible portion is arranged in the completed device such that application of pressurised gas to the airway tube urges the ventral wall portion of the soft, flexible portion into contact with the tissues surrounding the laryngeal opening or the anterior pharyngeal wall to thereby form a seal with the larynx when the mask portion is positioned in the laryngo pharynx to thereby prevent ingress of extraneous fluids into the larynx.

13. A device for maintaining an airway in a patient, the device comprising:

a mask portion; and an airway tube connected to or formed with the mask portion for passing gas to the patient's larynx when the mask portion is properly inserted into the laryngo pharynx;

the mask portion having an opening through which ventilation gases exit the mask portion, the mask portion further comprising a soft, flexible portion positioned on a ventral side of the mask portion, the soft, flexible portion having a part that extends from a structure comprising thicker wall thickness or less flexibility than the soft, flexible portion, the soft, flexible portion including a ventral wall portion positioned such that when the mask portion is inserted into a patient, the ventral wall portion lies generally parallel to the tissues surrounding the laryngeal inlet of the patient, the soft, flexible portion further comprising an inner wall that extends in a dorsal direction from the ventral wall portion; and a cricoid contacting portion that extends towards the cricoid cartilage and abuts with the cricoid cartilage when the mask portion is properly inserted, the cricoid contacting portion being adapted to form a seal in the vicinity of the cricoid cartilage or upper oesophagus, wherein the cricoid contacting portion, with a distal portion of the soft, flexible portion is in the form of a sling shaped region into which the cricoid cartilage snugly fits;

whereby the soft, flexible portion is arranged in the completed device such that application of pressurised gas to the airway tube urges the ventral wall portion of the soft, flexible portion into contact with the tissues surrounding the laryngeal opening or the anterior pharyngeal wall to thereby form a seal with the larynx when the mask portion is positioned in the laryngo pharynx to thereby prevent ingress of extraneous fluids into the larynx.

14. A device for maintaining an airway in a patient, the device comprising:

a mask portion; and an airway tube connected to or formed with the mask portion for passing gas to the patient's larynx when the mask portion is properly inserted into the laryngo pharynx;

the mask portion having an opening through which ventilation gases exit the mask portion, the mask portion further comprising a soft, flexible portion positioned on a ventral side of the mask portion, the soft flexible portion having a part that extends from a structure comprising thicker wall thickness or less flexibility than the soft, flexible portion, the soft, flexible portion including a ventral wall portion positioned such that when the mask portion is inserted into a patient, the ventral wall portion lies generally parallel to the tissues surrounding the laryngeal inlet of the patient, the soft flexible portion further comprising an inner wall that extends in a dorsal direction from the ventral wall portion, the opening being defined by a dorsal end of the inner wall, wherein an entire peripheral extent of the opening is dorsally spaced from the larynx when the device is properly inserted into the patient, and whereby the soft, flexible portion is arranged in the completed device such that application of pressurised gas to the airway tube urges the ventral wall portion of the soft, flexible portion into contact with the tissues surrounding the laryngeal opening or the anterior pharyngeal wall to thereby form a seal with the larynx when the mask portion is positioned in the laryngo pharynx to thereby prevent ingress of extraneous fluids into the larynx and wherein the pressurised gas also pushes the inner wall outwards and urges the inner wall into sealing contact with tissues underlying the inner wall;

wherein a distal end of a ventral peripheral portion of the mask portion includes an upwardly extending portion that extends towards a dorsal side of the mask portion and the upwardly extending portion includes one or more openings formed therein to facilitate fluid flow from the oesophagus to a proximal side of the mask portion during use of the mask portion.

15. The device as claimed in claim 14, wherein the mask portion is provided with a dorsal groove or recess near a distal tip thereof.

16. The device as claimed in claim 14, wherein a peripheral portion of the mask portion includes an inflatable cuff, with the soft, flexible portion extending from the inflatable cuff.

* * * * *